US010441723B2

(12) United States Patent
Nazzaro

(10) Patent No.: US 10,441,723 B2
(45) Date of Patent: Oct. 15, 2019

(54) VARIABLE FILL DRUG DELIVERY DEVICE

(71) Applicant: Insulet Corporation, Acton, MA (US)

(72) Inventor: David Nazzaro, Groveland, MA (US)

(73) Assignee: Insulet Corporation, Acton, MA (US)

( * ) Notice: Subject to any disclaimer, the term of this patent is extended or adjusted under 35 U.S.C. 154(b) by 0 days.

(21) Appl. No.: 15/676,289

(22) Filed: Aug. 14, 2017

(65) Prior Publication Data

US 2018/0043089 A1    Feb. 15, 2018

Related U.S. Application Data

(60) Provisional application No. 62/374,881, filed on Aug. 14, 2016, provisional application No. 62/375,026, (Continued)

(51) Int. Cl.
*A61M 5/145* (2006.01)
*A61M 5/142* (2006.01)
(Continued)

(52) U.S. Cl.
CPC ...... *A61M 5/31568* (2013.01); *A61M 5/1452* (2013.01); *A61M 5/1454* (2013.01);
(Continued)

(58) Field of Classification Search
CPC ............ A61M 5/14248; A61M 5/1454; A61M 5/31568; A61M 5/2033; A61M 5/1452;
(Continued)

(56) References Cited

U.S. PATENT DOCUMENTS

| 1,441,508 A | 1/1923 | Marius et al. |
|---|---|---|
| 3,885,662 A | 5/1975 | Schaefer |

(Continued)

FOREIGN PATENT DOCUMENTS

| CA | 606281 A | 10/1960 |
|---|---|---|
| DE | 4200595 A1 | 7/1993 |

(Continued)

OTHER PUBLICATIONS

Lind, et al.,"Linear Motion Miniature Actuators." Paper presented at the 2nd Tampere International Conference on Machine Automation, Tampere, Finland (Sep. 1998) 2 pages.
(Continued)

*Primary Examiner* — Theodore J Stigell

(57) ABSTRACT

Variable fill drug delivery devices for delivering a therapeutic agent to a patient are provided. A variable fill drug delivery device includes a drug container to store a variable amount (or user-selectable amount) of a therapeutic agent. A plunger of the variable fill drug delivery device is positioned in the drug container. An infusion engine of the variable fill device is coupled to the plunger. The infusion engine retains the plunger prior to activation of the variable fill drug delivery device and releases the plunger after activation of the variable fill drug delivery device. After activation, the infusion engine drives the plunger from a first position within the drug container to a second position within the drug container to expel the variable amount of the therapeutic agent from the drug container for delivery to a patient.

21 Claims, 25 Drawing Sheets

Related U.S. Application Data filed on Aug. 15, 2016, provisional application No. 62/385,749, filed on Sep. 9, 2016, provisional application No. 62/449,845, filed on Jan. 24, 2017, provisional application No. 62/449,849, filed on Jan. 24, 2017.

(51) Int. Cl.
*A61M 5/20* (2006.01)
*A61M 5/315* (2006.01)

(52) U.S. Cl.
CPC ...... *A61M 5/14248* (2013.01); *A61M 5/2033* (2013.01); *A61M 5/3155* (2013.01); *A61M 2202/0468* (2013.01); *A61M 2205/3306* (2013.01); *A61M 2205/3317* (2013.01); *A61M 2205/3379* (2013.01); *A61M 2205/581* (2013.01); *A61M 2205/582* (2013.01); *A61M 2205/583* (2013.01); *A61M 2205/584* (2013.01)

(58) Field of Classification Search
CPC ...... A61M 2005/14252; A61M 5/3155; A61M 2005/14533; A61M 2005/31518; A61M 2005/2073
See application file for complete search history.

(56) References Cited

U.S. PATENT DOCUMENTS

| | | |
|---|---|---|
| 3,946,732 A | 3/1976 | Hurscham |
| 4,108,177 A | 8/1978 | Pistor |
| 4,268,150 A | 5/1981 | Chen |
| 4,313,439 A | 2/1982 | Babb et al. |
| 4,424,720 A | 1/1984 | Bucchianeri |
| 4,435,173 A | 3/1984 | Siposs et al. |
| 4,498,843 A | 2/1985 | Schneider et al. |
| 4,507,115 A | 3/1985 | Kambara et al. |
| 4,551,134 A | 11/1985 | Slavik et al. |
| 4,562,751 A | 1/1986 | Nason et al. |
| 4,585,439 A | 4/1986 | Michel |
| 4,601,707 A | 7/1986 | Albisser et al. |
| 4,634,427 A | 1/1987 | Hannula et al. |
| 4,678,408 A | 7/1987 | Nason et al. |
| 4,684,368 A | 8/1987 | Kenyon |
| 4,755,169 A | 7/1988 | Samoff et al. |
| 4,898,579 A | 2/1990 | Groshong et al. |
| 4,944,659 A | 7/1990 | Labbe et al. |
| 4,969,874 A | 11/1990 | Michel et al. |
| 5,007,458 A | 4/1991 | Marcus et al. |
| 5,062,841 A | 11/1991 | Siegel |
| 5,205,819 A | 4/1993 | Ross et al. |
| 5,213,483 A | 5/1993 | Flaherty et al. |
| 5,261,882 A | 11/1993 | Sealfon |
| 5,281,202 A | 1/1994 | Weber et al. |
| 5,346,476 A | 9/1994 | Elson |
| 5,364,342 A | 11/1994 | Beuchat et al. |
| 5,433,710 A | 7/1995 | VanAntwerp et al. |
| 5,582,593 A | 12/1996 | Hultman |
| 5,637,095 A | 6/1997 | Nason et al. |
| 5,665,070 A | 9/1997 | McPhee |
| 5,713,875 A | 2/1998 | Tanner, II |
| 5,747,350 A | 5/1998 | Saltier |
| 5,748,827 A | 5/1998 | Holl et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,807,075 A | 9/1998 | Jacobsen et al. |
| 5,839,467 A | 11/1998 | Saaski et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,957,890 A | 9/1999 | Mann et al. |
| 5,961,492 A | 10/1999 | Kriesel et al. |
| 6,019,747 A | 2/2000 | McPhee |
| 6,174,300 B1 | 1/2001 | Kriesel et al. |
| 6,190,359 B1 | 2/2001 | Heruth |
| 6,200,293 B1 | 3/2001 | Kriesel et al. |
| 6,363,609 B1 | 4/2002 | Pickren |
| 6,375,638 B2 | 4/2002 | Nason et al. |
| 6,474,219 B2 | 11/2002 | Klitmose et al. |
| 6,485,461 B1 | 11/2002 | Mason et al. |
| 6,485,462 B1 | 11/2002 | Kriesel |
| 6,488,652 B1 | 12/2002 | Weijand et al. |
| 6,520,936 B1 | 2/2003 | Mann |
| 6,527,744 B1 | 3/2003 | Kriesel et al. |
| 6,537,249 B2 | 3/2003 | Kriesel et al. |
| 6,569,115 B1 | 5/2003 | Barker et al. |
| 6,595,956 B1 | 7/2003 | Gross et al. |
| 6,656,158 B2 | 12/2003 | Mahoney et al. |
| 6,699,218 B2 | 3/2004 | Flaherty et al. |
| 6,723,072 B2 | 4/2004 | Flaherty et al. |
| 6,883,778 B1 | 4/2005 | Newton et al. |
| 7,144,384 B2 | 12/2006 | Gorman et al. |
| 7,160,272 B1 | 1/2007 | Eyal et al. |
| 7,914,499 B2 | 3/2011 | Gonelli et al. |
| 8,382,703 B1 | 2/2013 | Abdelaal et al. |
| 8,939,935 B2 | 1/2015 | O'Connor et al. |
| 9,180,244 B2 | 11/2015 | Anderson et al. |
| 9,192,716 B2 | 11/2015 | Jugl et al. |
| 9,402,950 B2 | 8/2016 | DiIanni et al. |
| 2001/0056258 A1 | 12/2001 | Evans |
| 2002/0173769 A1 | 11/2002 | Gray et al. |
| 2003/0040715 A1 | 2/2003 | D'Antonio et al. |
| 2004/0064088 A1 | 4/2004 | Gorman et al. |
| 2004/0068224 A1 | 4/2004 | Couvillon, Jr. et al. |
| 2004/0069044 A1 | 4/2004 | Lavi et al. |
| 2005/0020980 A1 | 1/2005 | Inoue et al. |
| 2005/0203461 A1 | 9/2005 | Flaherty et al. |
| 2005/0238507 A1 | 10/2005 | DiIanni et al. |
| 2006/0041229 A1 | 2/2006 | Garibotto et al. |
| 2006/0079765 A1 | 4/2006 | Neer et al. |
| 2006/0178633 A1 | 8/2006 | Garibotto et al. |
| 2008/0114304 A1 | 5/2008 | Nalesso et al. |
| 2008/0172028 A1 | 7/2008 | Blomquist |
| 2009/0024083 A1 | 1/2009 | Kriesel et al. |
| 2010/0036326 A1 | 2/2010 | Matusch |
| 2010/0241066 A1 | 9/2010 | Hansen et al. |
| 2011/0144586 A1 | 6/2011 | Michaud et al. |
| 2013/0245545 A1 | 9/2013 | Arnold et al. |
| 2014/0018730 A1 | 1/2014 | Muller-Pathle |
| 2014/0142508 A1 | 5/2014 | DiIanni et al. |
| 2014/0171901 A1 | 6/2014 | Langsdorf et al. |
| 2015/0041498 A1 | 2/2015 | Kakiuchi et al. |
| 2015/0202386 A1 | 7/2015 | Brady et al. |
| 2015/0290389 A1 | 10/2015 | Nessel |
| 2015/0297825 A1 | 10/2015 | Focht et al. |
| 2017/0021096 A1 | 1/2017 | Cole et al. |
| 2017/0021137 A1 | 1/2017 | Cole |
| 2017/0239415 A1 | 8/2017 | Hwang et al. |

FOREIGN PATENT DOCUMENTS

| | | |
|---|---|---|
| EP | 0867196 A2 | 9/1998 |
| EP | 1177802 A1 | 2/2002 |
| EP | 2468338 A1 | 6/2012 |
| EP | 2703024 A1 | 3/2014 |
| FR | 2096275 A5 | 2/1972 |
| FR | 2455269 A1 | 11/1980 |
| GB | 357139 A1 | 9/1931 |
| GB | 810488 A | 3/1959 |
| GB | 2549750 A | 11/2017 |
| IL | 46017 A | 11/1977 |
| JP | H08238324 A | 9/1996 |
| NL | 1019126 C1 | 4/2003 |
| WO | 8101658 A1 | 6/1981 |
| WO | 8606796 A1 | 11/1986 |
| WO | 9855073 A1 | 12/1998 |
| WO | 9910040 A1 | 3/1999 |

(56) References Cited

FOREIGN PATENT DOCUMENTS

| WO | 9910049 | A1 | | 3/1999 |
|---|---|---|---|---|
| WO | 9962576 | A1 | | 12/1999 |
| WO | 200178812 | A1 | | 10/2001 |
| WO | 200226282 | A2 | | 4/2002 |
| WO | 2002076535 | A1 | | 10/2002 |
| WO | 2003097133 | A1 | | 11/2003 |
| WO | WO2003097133 | | * | 11/2003 |
| WO | 2007066152 | A2 | | 6/2007 |
| WO | 2009039203 | A2 | | 3/2009 |
| WO | 2010139793 | A1 | | 12/2010 |
| WO | 2011033823 | A1 | | 6/2011 |
| WO | 2011075042 | A1 | | 6/2011 |
| WO | 2012073032 | A1 | | 6/2012 |
| WO | 2013050535 | A2 | | 4/2013 |
| WO | 2014149357 | A1 | | 9/2014 |
| WO | 2015081337 | A2 | | 6/2015 |
| WO | 2015117854 | A1 | | 8/2015 |
| WO | 2015167201 | A1 | | 11/2015 |
| WO | 2015177082 | A1 | | 11/2015 |
| WO | 2017187177 | A1 | | 11/2017 |

OTHER PUBLICATIONS

Author unknown, "The Animas R-1000 Insulin Pump—Animas Corporation intends to exit the insulin pump business and discontinue the manufacturing and sale of Animas® Vibe® and OneTouch Ping® insulin pumps." [online], Dec. 1999 [retrieved on Oct. 16, 2018]. Retrieved from the Internet URL: http://www.animaspatientsupport.com/.

Author unknown, CeramTec "Discover the Electro Ceramic Products CeramTec acquired from Morgan Advanced Materials" [online], Mar. 1, 2001 [retrieved on Oct. 17, 2018]. Retrieved from the Internet URL: http://www.morgantechnicalceramics.com/, 2 pages.

Vaughan, M.E., "The Design, Fabrication, and Modeling of a Piezoelectric Linear Motor." Master's thesis, Virginia Polytechnic Institute and State University, VA. (2001).

Galante, et al., "Design, Modeling, and Performance of a High Force Piezoelectric Inchworm Motor," Journal of Intelligent Material Systems and Structures, vol. 10, 962-972 (1999).

International Search Report and Written Opinion for application No. PCT/US2017/034811, dated Oct. 18, 2017, 15 pages.

International Search Report and Written Opinion for application No. PCT/US17/46508 dated Jan. 17, 2018, 14 pages.

International Search Report and Written Opinion for application No. PCT/US17/46777, dated Dec. 13, 2017 14 pages.

International Search Report and Written Opinion for application No. PCT/US17/46737, dated Dec. 14, 2017 11 pages.

International Search Report and Written Opinion for application No. PCT/US17/55054, dated Jan. 25, 2018 13 pages.

International Search Report and Written Opinion for PCT/US2018/014351, dated Jun. 4, 2018, 11 pages.

International Search Report and Written Opinion for application No. PCT/US18/45155, dated Oct. 15, 2018, 15 pages.

International Search Report and Written Opinion for application No. PCT/US2017/34814, dated Oct. 11, 2017, 16 pages.

International Search Report and Written Opinion for International Application No. PCT/US2019/035756, dated Jul. 31, 2019, 10 pages.

* cited by examiner

VARIABLE FILL DRUG DELIVERY DEVICE

CROSS-REFERENCE TO RELATED APPLICATIONS

This application claims the benefit of U.S. Provisional Application No. 62/374,881, filed Aug. 14, 2016, U.S. Provisional Application No. 62/375,026, filed Aug. 15, 2016, U.S. Provisional Application No. 62/385,749, filed Sep. 9, 2016, U.S. Provisional Application No. 62/449,845, filed Jan. 24, 2017, and U.S. Provisional Application No. 62/449,849, filed Jan. 24, 2017, each of which is incorporated herein by reference in its entirety.

TECHNICAL FIELD

Embodiments generally relate to medication delivery. More particularly, embodiments relate to wearable drug delivery devices.

BACKGROUND

Many conventional drug delivery devices are provided to a patient without a liquid drug prefilled in a drug container of the device. The patient is therefore often required to fill the drug device prior to use. These conventional drug delivery devices can typically include unreliable complex systems for expelling the liquid drug from the drug device, thereby increasing the costs to the user. Further, these conventional drug delivery devices often do not allow a variable amount (or user-selectable amount) of liquid drug to be inserted into the drug container so that the patient can vary dosages. Accordingly, there is a need for an improved drug delivery device that allows for variable filling and expels the stored liquid drug in a less costly but more reliable manner.

DETAILED DESCRIPTION

This disclosure presents various systems, components, and methods related to a wearable drug delivery device. Each of the systems, components, and methods disclosed herein provides one or more advantages over conventional systems, components, and methods.

Various embodiments include a variable fill drug delivery device. The variable fill drug delivery device includes a drug container to store a variable amount (or user-selectable amount) of a therapeutic agent. A plunger of the variable fill drug delivery device is positioned in the drug container. An infusion engine of the variable fill device is coupled to the plunger. The infusion engine retains the plunger prior to activation of the variable fill drug delivery device and releases the plunger after activation of the variable fill drug delivery device. After activation, the infusion engine drives the plunger from a first position within the drug container to a second position within the drug container to expel the variable amount of the therapeutic agent from the drug container for delivery to a patient. Other embodiments are disclosed and described.

Figure 1:
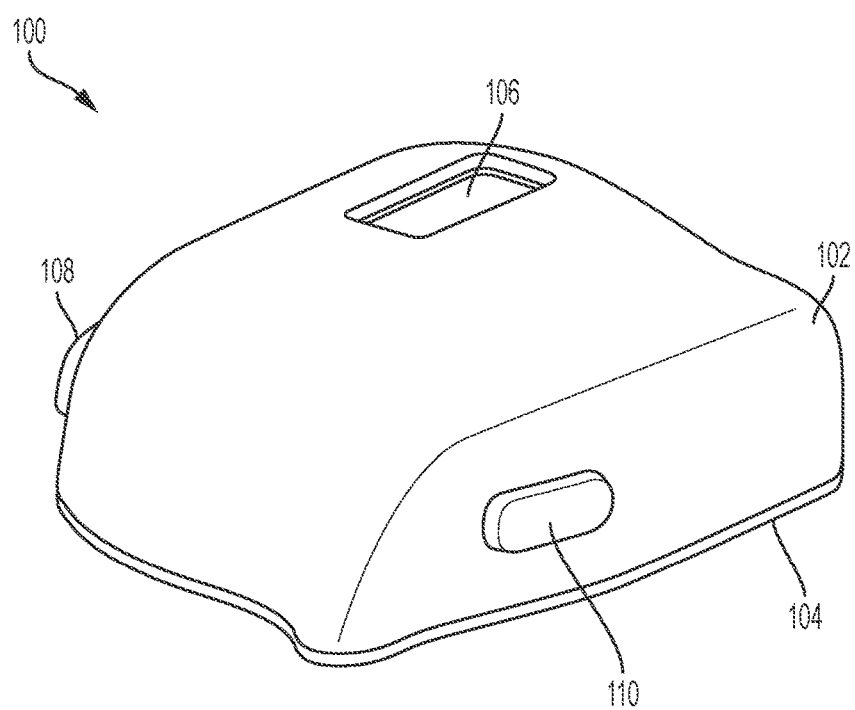
FIG. 1 illustrates a first isometric view of a first exemplary embodiment of a variable fill drug delivery device.

FIG. 1 illustrates a first exemplary embodiment of a variable fill drug delivery device 100. FIG. 1 shows the variable fill drug delivery device 100 in a first isometric view. The drug delivery device 100 can include an upper portion or upper housing component 102 and a lower portion or a lower housing component 104. The upper housing component 102 can be coupled to the lower housing component 104. In various embodiments, internal components of the drug delivery device 100 can be coupled to an interior surface of the lower housing component 104. The lower housing component 104 can be a base of the drug delivery device 100 and the upper housing component 102 can be fitted onto the lower housing component 104 as a cover of the drug delivery device 100.

The upper housing component 102 can include a window or viewing area 106. The window 106 can be positioned over a drug container positioned within the drug delivery device 100. The window 106 can enable a patient to view an amount of liquid drug or other agent stored in the drug container. The window 106 can comprise a transparent plastic material or can be a cutout or opening of the upper housing component 102.

The upper housing component 102 can further include a first user interaction feature or component 108 and a second user interaction feature or component 110. The first and second user interaction features 108 and 110 can be, for example, pushbuttons, slide buttons, or other touch sensitive components that can be manipulated by a patient. The first and second user interaction features 108 and 110 can be used by a patient to selectively activate the drug delivery device 100 as described in more detail herein.

The drug delivery device 100 can be of any size and shape and is not limited to the form factor illustrated in FIG. 1. The size and shape of the drug delivery device 100 can vary based on the size of the drug container. The upper housing component 102 and the lower housing component 104 can be formed of a plastic material, though it will be appreciated by one of ordinary skill in the art that other appropriate materials can be used.

The drug delivery device 100 can be provided to a patient unfilled. That is, the drug delivery device 100 can be provided to a patient with an empty drug container. In various embodiments, the patient can be required to fill the drug delivery device 100 through a fill port with a liquid drug or other agent prior to use. Though not shown in this view, in various embodiments, a fill port can be provided on the lower housing component 104. The drug delivery device 100 allows the patient to fill a desired amount (e.g., a user-selected amount) of liquid drug or other agent into the drug container. In particular, an amount of liquid drug or other agent that is less than an amount of liquid drug or other agent that the drug container is capable of storing may be placed into the drug container.

For example, the drug container of the drug delivery device 100 may be capable of or configured to store a total fixed amount or volume of a liquid drug or other therapeutic agent. The patient or user of the drug delivery device 100 may choose to fill the drug container up to the total fixed amount or may choose to fill the drug container to an amount that is less than the total fixed amount. The amount of liquid drug or other agent the patient fills the drug container with can be considered a user-selectable amount of the liquid drug or other therapeutic agent. The user-selectable amount of the liquid drug or other therapeutic agent allows the patient or user to vary dose sizes. Accordingly, the drug delivery device 100 can be considered to be a variable fill drug delivery device with a container configured to store a user-selectable amount of liquid drug or other therapeutic agent.

The drug delivery device 100 can generally be used to deliver any type of drug or agent to a patient. In general, and for purposes of the description of the drug delivery device 100 provided herein, the drug delivery device 100 can be considered to hold and deliver a therapeutic agent to a patient, which can include any liquid drug and/or biologic. The drug delivery device 100 can be intended for a single use and can be disposable but is not so limited. In various embodiments, the drug delivery device 100 can be reusable and/or can be intended for multiple injections with or without the need to refill the drug container with liquid drug or other agent. The drug delivery device 100 can be intended to provide a liquid drug or other agent to the patient in a single bolus over a predetermined amount of time (e.g., from a few minutes up to an hour or so). The drug delivery device 100 can alternatively be used to provide a liquid drug or other agent to the patient in multiple doses over a predetermined period of time.

In various embodiments, the drug delivery device 100 can be an entirely mechanical system. In various embodiments, the drug delivery device 100 can be implemented as an electromechanical system. In various embodiments, the drug delivery system 100 can be a wearable drug delivery device. For example, a bottom surface of the drug delivery device 100 (e.g., an outer surface of the lower housing component 104) can include an adhesive that can be used to couple the drug delivery device 100 to the patient (e.g., after filling the drug container of the drug delivery device 100). Once attached to the patient, the drug delivery device 100 can be activated (e.g., by manipulating the first and second user interaction features 108 and 110) such that the stored liquid drug or agent is provided to the patient.

Figure 2:
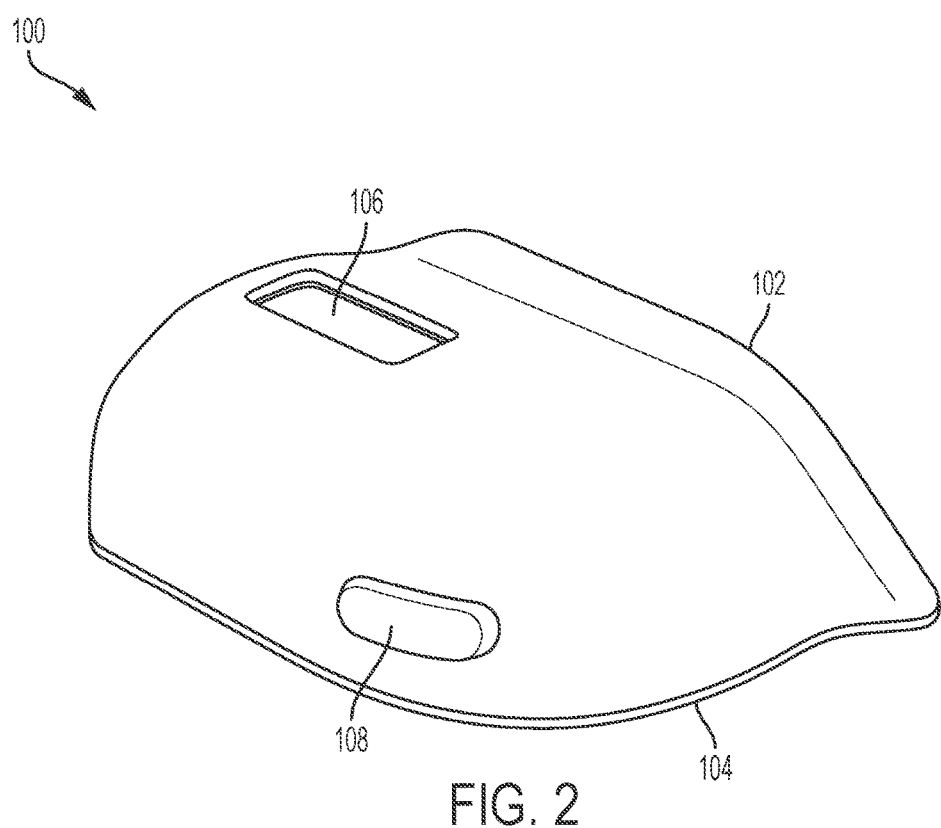
FIG. 2 illustrates a second isometric view of the drug delivery device depicted in FIG. 1.

FIG. 2 illustrates a second view of the drug delivery device 100. FIG. 2 shows the drug delivery device 100 in a second isometric view. FIG. 2 further shows the exemplary form factor of the drug delivery device 100 and shows an exemplary arrangement of the window 106 and the first user interaction feature 108 on the upper housing component 102.

Figure 3:
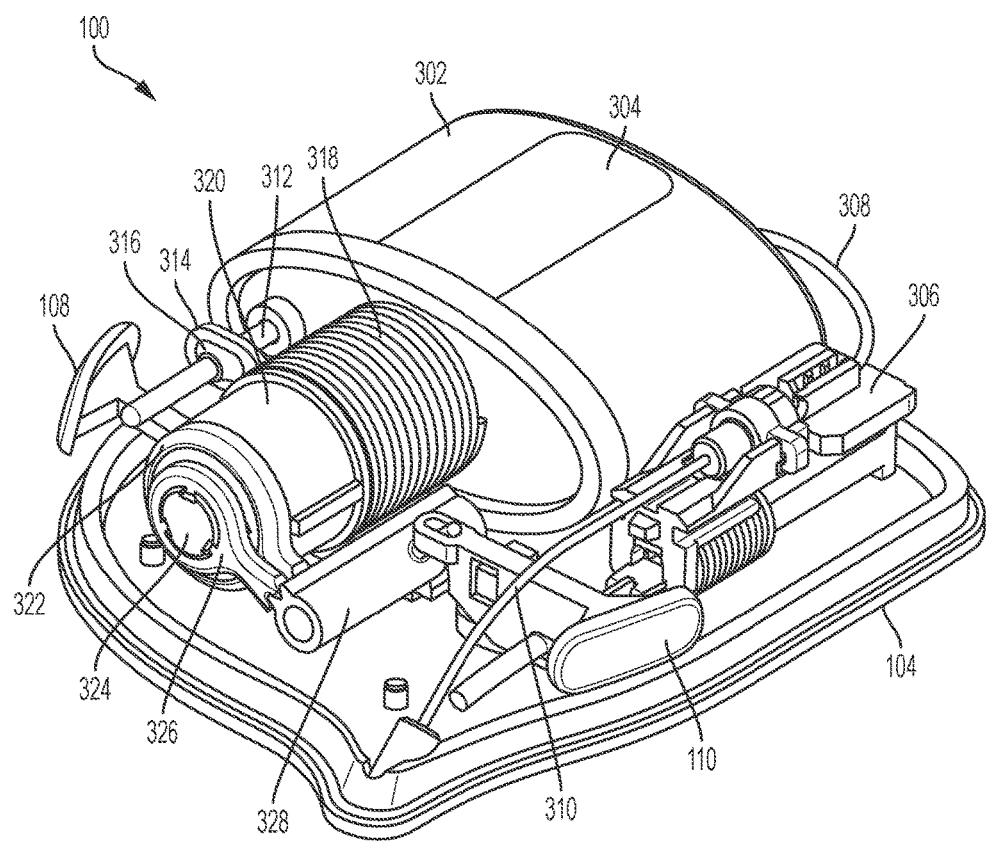
FIG. 3 illustrates internal components of the drug delivery device depicted in FIG. 1.

FIG. 3 illustrates the drug delivery device 100 without the upper housing component 102. FIG. 3 shows an exemplary arrangement of internal components of the drug delivery device 100. The internal components of the drug delivery device 100 can be arranged on and coupled to an interior surface of the lower housing component 104.

As shown in FIG. 3, the drug delivery device 100 can include a drug container 302. The drug container 302 can hold or store any liquid drug or agent. The drug container 302 can be of any size and shape. As shown in FIG. 3, the drug container 302 can have an elliptical cross-sectional shape but is not so limited. The drug container 302 can include a window or viewing area 304. The window 304 can be formed of a transparent plastic material. The window 304 can be aligned with the window 106 of the upper housing component 102 to enable the patient to view an amount of liquid drug or agent contained in the drug container 302.

The drug container 302 can be coupled to a needle insertion component 306. The needle insertion component 306 can be coupled to the drug container 302 by a needle conduit 308. The needle conduit 308 can be, for example, metal or plastic tubing. An amount of liquid drug or other agent that is expelled from the drug container 302 can be provided to the needle insertion component 306 by way of the needle conduit 308.

The needle insertion component 306 can be coupled to a needle 310. The needle 310 can deliver the expelled liquid drug or other agent to the patient. The needle insertion component 306 can operate to insert the needle 310 into the patient and to route the expelled liquid drug or other agent from the drug container 302 to the needle 310. In various embodiments, when the drug delivery device 100 is initially activated (e.g., by a patient manipulating the first and/or second user interaction features 108 and 110), the needle insertion component 306 can cause the needle 310 to be advanced so that at least a portion of the needle 310 can be inserted into the patient, enabling a liquid drug or other agent stored in the drug container 302 to be subsequently delivered to the patient. To access the patient, an end of the needle 310 can extend outside of the drug delivery device 100 (e.g., beyond an outer surface of the lower housing component 104).

The drug delivery device 100 includes a number of components that interact during the filling of the drug container 302 and that interact as the liquid drug or other agent in the drug container 302 is expelled for delivery to the patient. Generally, a plunger (not shown in FIG. 2) positioned within the drug container 302 can be used to expel the liquid drug or other agent from the drug container 302. Components of the drug delivery device 100, as further described herein, can be used to operate the plunger to expel the liquid drug or other agent from the drug container.

As shown in FIG. 3, the drug delivery device 100 can include a fill rod 312, a fill lever 314, and a boot connector 316. The fill lever 314 can be coupled to the fill rod 312 by the boot connector 316. The boot connector 316 can be formed from an elastomeric material. The drug delivery device 100 can further include a first compression spring 318, a flexure beam housing 320, a clutch lock 322, a fixed thrust component 324, a release component 326, and a tube gear 328. Each of these constituent components of the drug delivery device 100 are described in more detail herein.

Figure 4:
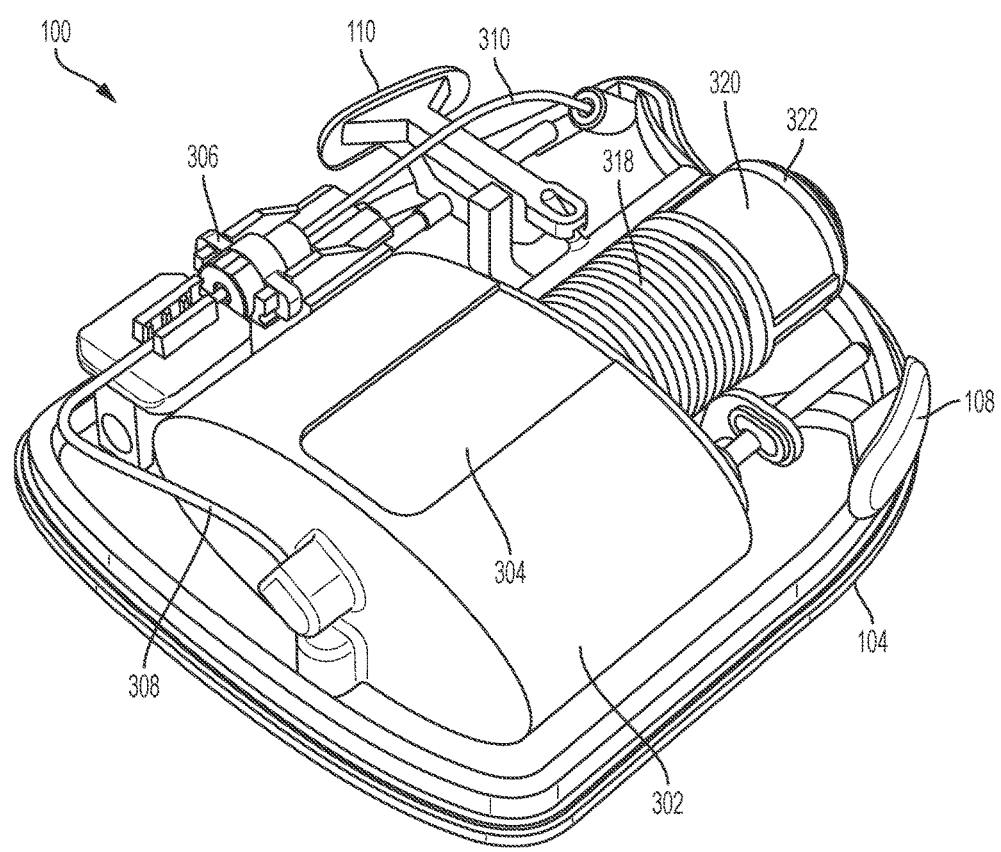
FIG. 4 illustrates a second view of the internal components of the drug delivery device depicted in FIG. 3.

FIG. 4 illustrates a second view of the drug delivery device 100 as depicted in FIG. 3. In particular, FIG. 4 shows a back view of the drug delivery device 100 with the upper housing component 102 removed. As shown in FIG. 4, the needle conduit 308 can be fluidly coupled to the drug container 302 to receive a liquid drug or other agent expelled from the drug container 302. The needle conduit 308 can then provide the expelled liquid drug or other agent to the needle insertion component 306 for delivery to the patient through the needle 310.

Figure 5:
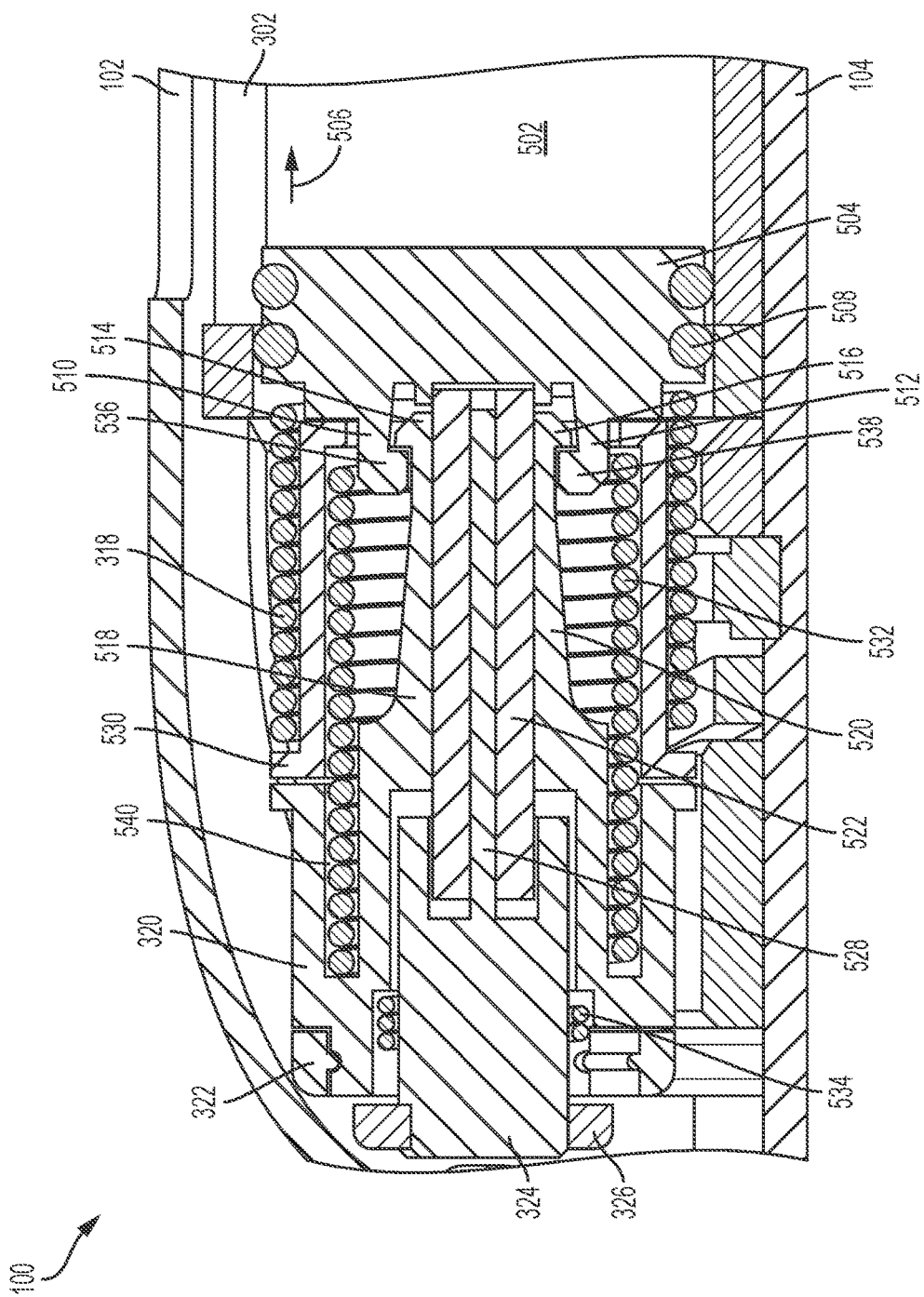
FIG. 5 illustrates a first cross-sectional view of a portion of the drug delivery device depicted in FIG. 1.

FIG. 5 illustrates a cross-sectional view of a portion of the drug delivery device 100. The cross-sectional view of the portion of the drug delivery device 100 depicted in FIG. 5 is shown in reference to a cross-sectional view indicator 1720 depicted in FIG. 17, which illustrates an overhead view of a portion of the internal components of the drug delivery device depicted in FIG. 1. Each of the cross-sectional views described herein, for example, in reference to FIGS. 5, 7, 9, and 11-16, are made in reference to the cross-sectional view indicator 1720.

FIG. 5 shows an exemplary arrangement of various components of the drug delivery device 100. As shown in FIG. 5, the drug container 302 can include a reservoir 502 as an internal portion of the drug container 302. The reservoir 502 can hold or store the liquid drug or other agent to be provided to the patient. Adjacent to the reservoir 502 and extending into the reservoir can be a plunger 504. The plunger 504 can be moved in a direction 506 to expel a liquid drug or other agent from the reservoir 502. The reservoir 502 can be filled through a fill port (not shown in FIG. 5).

The plunger 504 can include one or more sealing features 508. The sealing features 508 can be formed of a plastic or elastomeric material and, in various embodiments, may comprise O-rings. The sealing features 508 can be positioned on an outer surface of the plunger 504 to form a seal between the plunger 504 and the internal surfaces of the drug container 302 that define the reservoir 502. The plunger 504 can have a cross-sectional shape matching a cross-sectional shape of the drug container 302 (e.g., the plunger 504 can have an elliptical cross-sectional shape matching an elliptical cross-section shape of the drug container 302 and reservoir 502).

The plunger 504 can include a first arm 510 and a second arm 512. The first and second arms 510 and 512 can be similarly sized and shaped. The first and second arms 510 and 512 can extend away from the plunger 504 in a direction away from the reservoir 502. The plunger 504 can be restricted from moving in the direction 506 by the interaction of a first depending tab portion 536 of the first arm 510 and a first plunger latch 514 and by interaction of a second depending tab portion 538 of the second arm 512 and a second plunger latch 516. The first plunger latch 514 can be positioned at an end of a first arm 518 of the flexure beam housing 320. The second plunger latch 516 can be positioned at an end of a second arm 520 of the flexure beam housing 320. The first and second arms 518 and 520 can be considered to be flexure beams of the flexure beam housing 320.

As shown in FIG. 5, the first plunger latch 514 can be positioned behind the first depending tab portion 536 of the first arm 510 (e.g., closer to the reservoir 502) and the second plunger latch 516 can be positioned behind the second depending tab portion 538 of the second arm 512 (e.g., closer to the reservoir 502) such that interaction between the first and second depending tab portions 536 and 538 and the first and second plunger latches 514 and 516, respectively, prevents the plunger 504 from moving in the direction 506. As described in detail further herein, the plunger 504 may be spring-biased to move in the direction 506. A release rod or release coupler 522 can be positioned between the first arm 518 and the second arm 520 to maintain the first and second plunger latches 514 and 516 in the positions as shown in FIG. 5. The release coupler 522 can also be coupled to the plunger 504. The first plunger latch 514 can be attached or coupled to the first arm 510 and the second plunger latch 516 can be attached or coupled to the second arm 512 via the first and second depending tab portions 536 and 538, respectively. The arrangement of the first and second plunger latches 514 and 516 relative to the first and second arms 510 and 512 as shown in FIG. 5 can restrict movement of the plunger 504 in the direction 506. In particular, the release coupler 522, as depicted in FIG. 5, can ensure the first and second plunger latches 514 and 516 are pressed up against and positioned behind the first and second depending tab portions 536 and 538 of the first and second arms 510 and 512, respectively, to restrict movement of the plunger 504 in the direction 506.

The release coupler 522 can be positioned around or over an arm or spline shaft 528 of the fixed thrust member 324. The spline shaft 528 can extend from a base of the fixed thrust member 324 toward the plunger 504. The spline shaft 528 and the release coupler 522 can together form a slip joint. In various embodiments, the spline shaft 528 and the release coupler 522 can be coupled together by a friction fit and/or a splined connection.

As further shown in FIG. 5, drug delivery device 100 can include a spring cap 530. A first end of the spring cap 530 can be positioned adjacent to the flexure beam housing 320. A second end of the spring cap 530 can be positioned adjacent to the plunger 504. The first compression spring 318 can be positioned around the spring cap 530. One end of the first compression spring 318 may engage a raised lip of the spring cap 530, while a second end of the first compression spring may engage a surface of the plunger 504 to bias the plunger in the direction of 506. A second compression spring 532 can be positioned around the first and second arms 518 and 520 and may be received within a recess portion 540 of the flexure beam housing 320 and positioned under the spring cap 530 as shown in FIG. 5. Thus, one end of the second compression spring 532 can engage a surface of the flexure beam housing 320 while a second end of the second compression spring can engage a surface of the spring cap 530 so that the spring cap 530 is biased toward the plunger 504.

The first and second compression springs 318 and 532 can be series compression springs. The first and second compression springs 318 and 532 can provide a high force and can have the same or substantially the same spring constant, k, values. In some embodiments the first and second compression springs 318, 532 can, alternatively, have different spring constant values. The drug delivery device 100 can further include a clutch spring 534, which can be disposed around a portion of the fixed thrust member 324. The clutch spring 534 can be a torsion spring. The clutch spring 534 can couple or lock the flexure beam housing 320 to the base of the fixed thrust member 324 as described further herein.

As shown in FIG. 5, the first and second compression springs 318 and 532 are in a compressed state. The first and second compression springs 318 and 532 are biased to expand longitudinally (e.g., with respect to the depiction of the drug delivery device 100 in FIG. 5). The first and second compression springs 318 and 532 are prevented from expanding due to the restricted movement of the plunger 504; specifically, due to the coupling of the first and second plunger latches 514 and 516 to the first and second depending tabs 536 and 538 of the first and second arms 510 and 512, respectively.

FIG. 5 illustrates the drug delivery device 100 in a filled state (e.g., in a substantially completely filled state). That is, FIG. 5 can represent the drug delivery device 100 when a liquid drug or other agent has been placed into the reservoir 502. In various embodiments, a patient can place an amount of liquid drug or other agent into the reservoir 502 through a fill port of the drug delivery device. The fill port can be positioned on the lower housing 104 (not shown in FIG. 5 for simplicity). FIG. 5 can further represent the drug delivery device 100 in a state prior to activation by a patient (e.g., prior to insertion of the needle 310 into a patient to enable delivery of the liquid drug or other agent to the patient).

Figure 14:
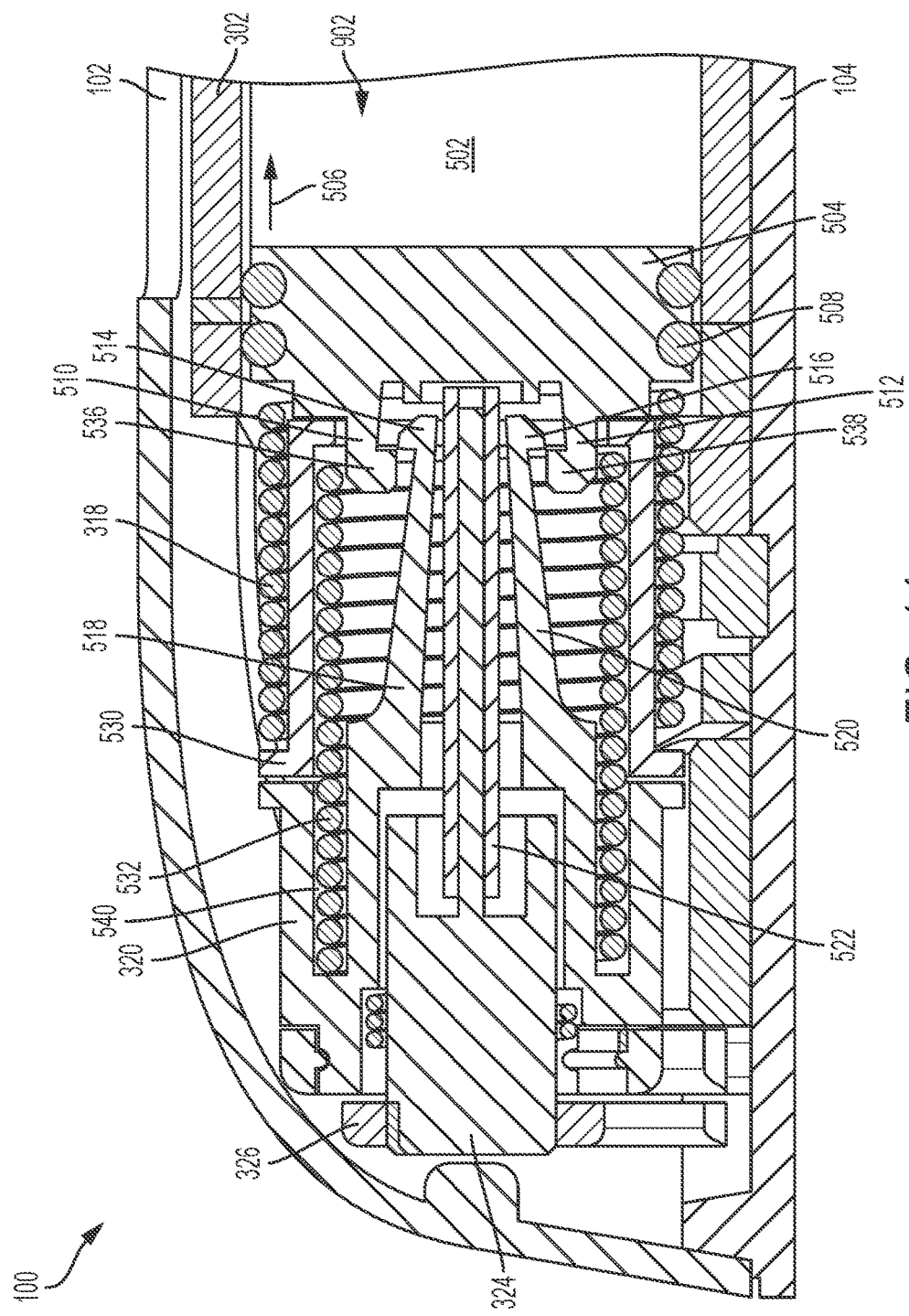
FIG. 14 illustrates a seventh cross-sectional view of a portion of the drug delivery device depicted in FIG. 1.
Figure 15:
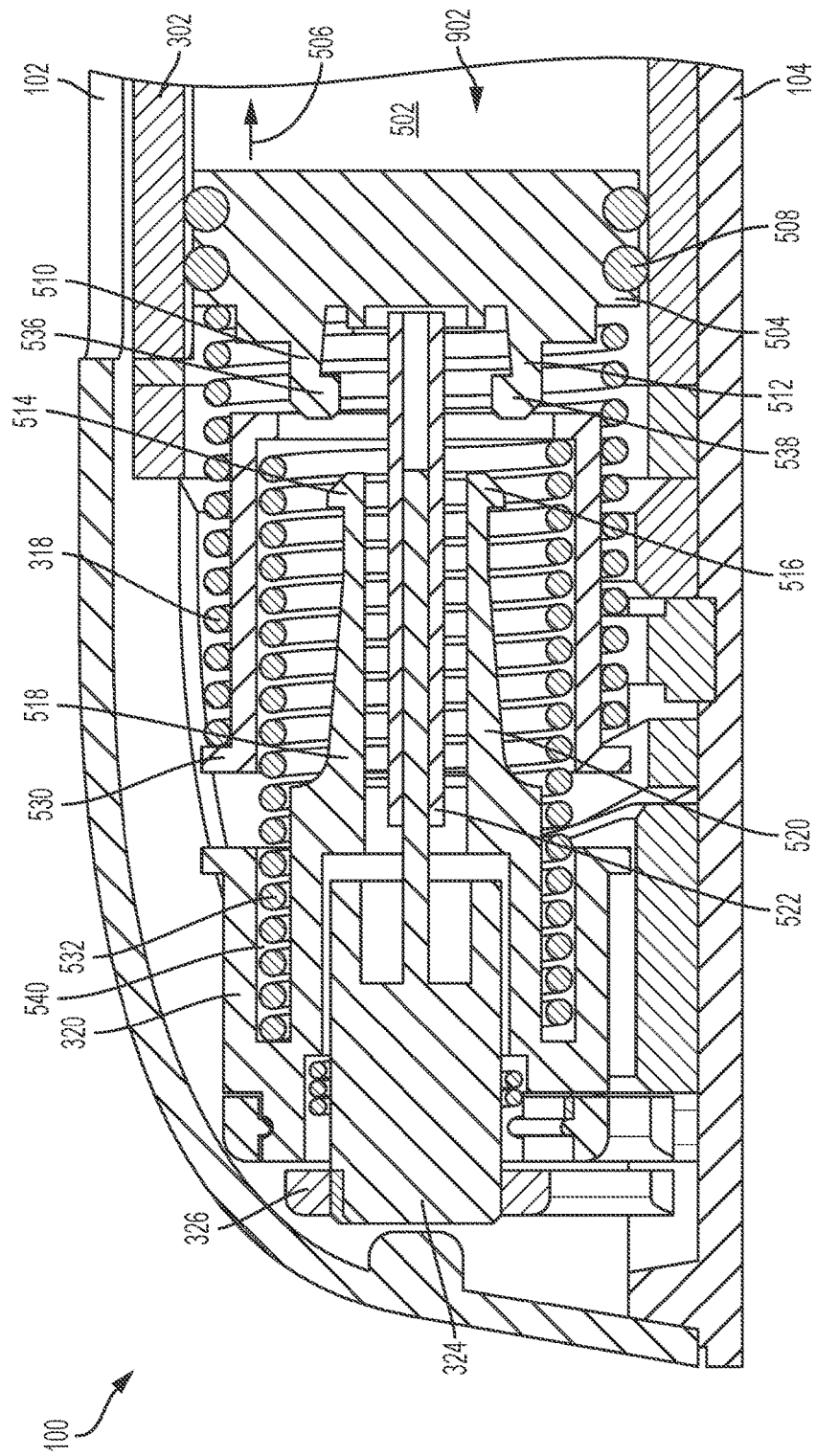
FIG. 15 illustrates an eighth cross-sectional view of a portion of the drug delivery device depicted in FIG. 1.
Figure 16:
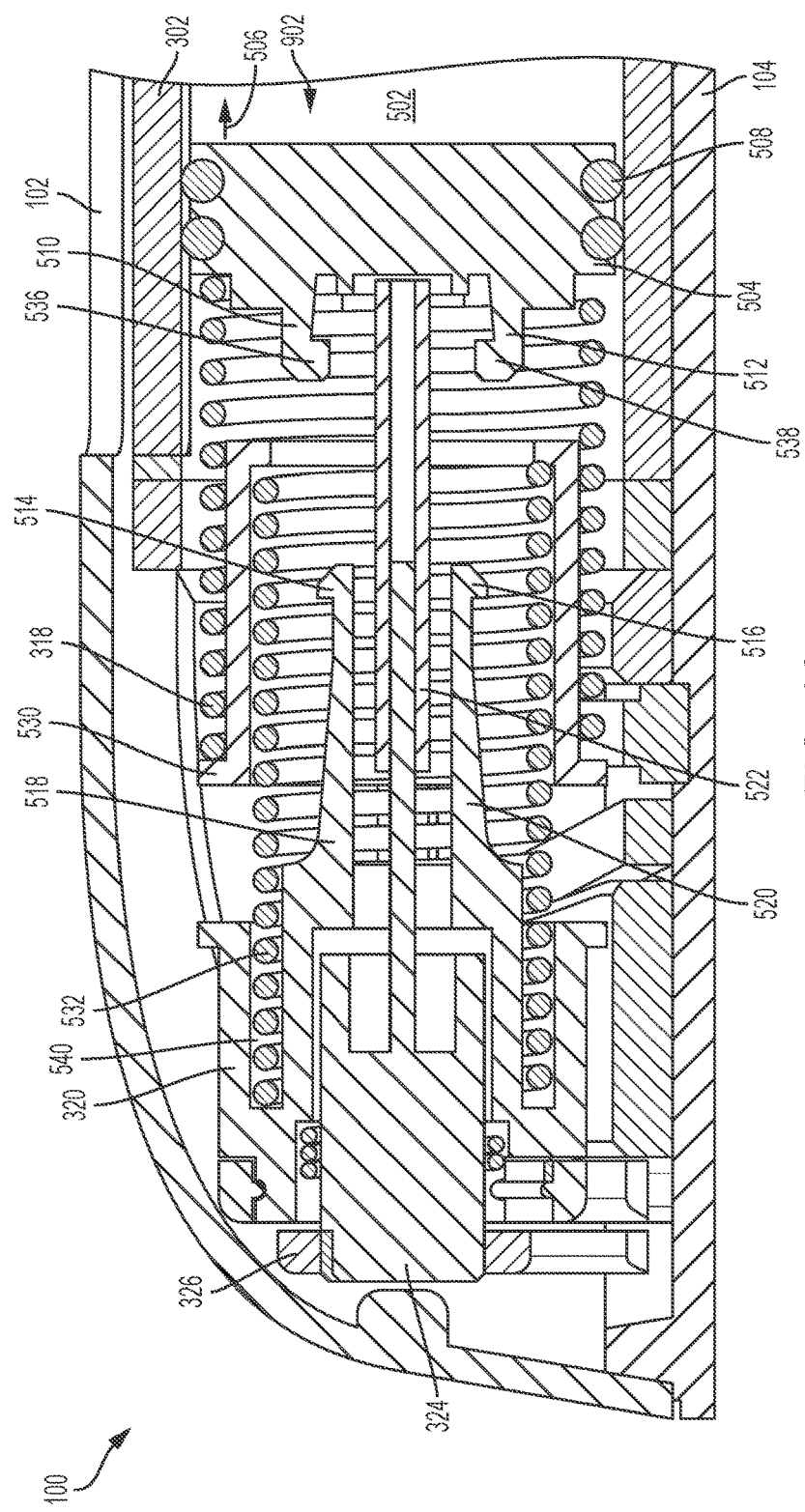
FIG. 16 illustrates a ninth cross-sectional view of a portion of the drug delivery device depicted in FIG. 1.

FIGS. 6-11 illustrate the drug delivery device 100 in various stages of being filled with a liquid drug or other agent. FIGS. 6-11 show the interaction of the components depicted in FIG. 5 as the drug container 302 begins in an initial empty state and ends in a final filled state. FIGS. 14-16 illustrate the drug delivery device 100 in various stages of being emptied—that is, as the plunger 504 expels the liquid drug or other agent from the reservoir 502. Accordingly, FIGS. 14-16 show the interaction of the components depicted in FIG. 5 as the drug container 302 begins in an initial filled state and ends in a final empty state after fully expelling any liquid drug or other agent previously stored in the reservoir 502.

Figure 6:
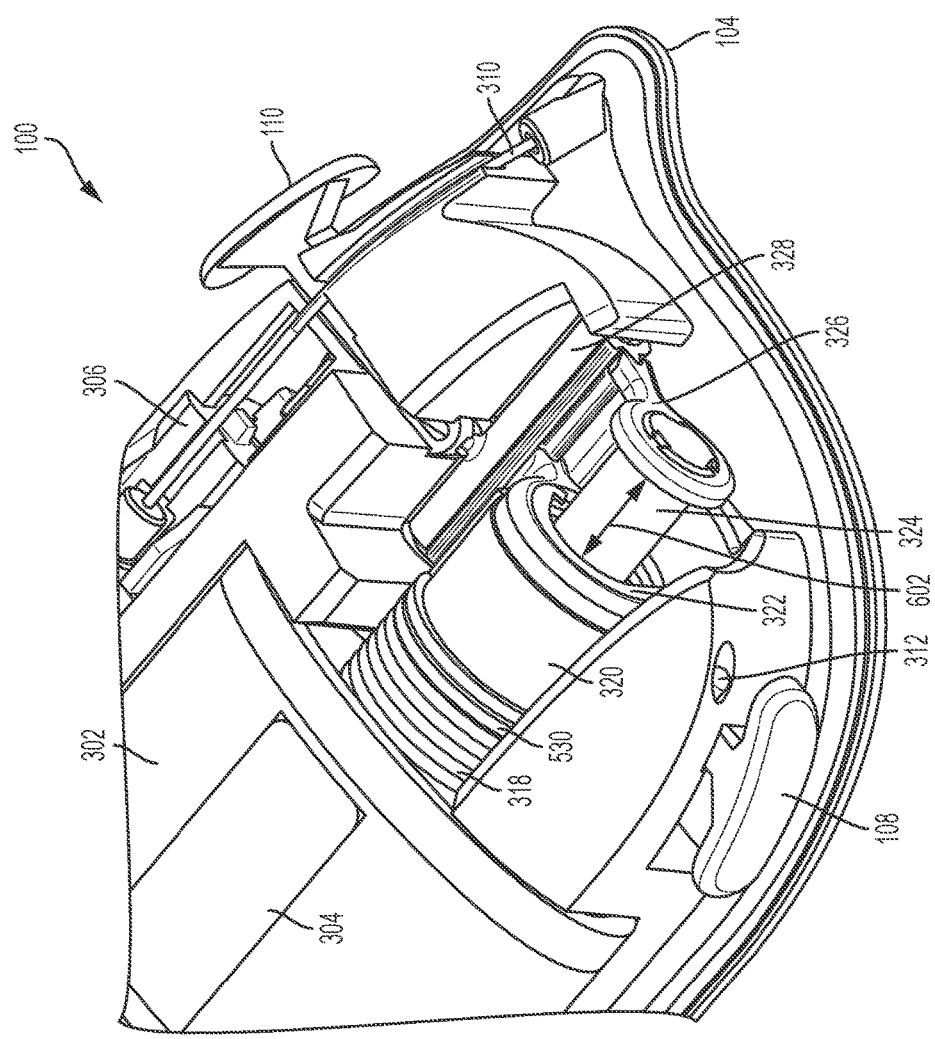
FIG. 6 illustrates a first overhead isometric view of a portion of the drug delivery device depicted in FIG. 1.

FIG. 6 illustrates an overhead or top view of the drug delivery device 100 without the top housing component 102. FIG. 6 shows the internal components of the drug delivery device 100 prior to the drug container 302 being filled with any liquid drug or other agent. As shown in FIG. 6, the first compression spring 318, the spring cap 530, the flexure beam housing 320, and the clutch lock 322 can be coupled together and can move together relative to the stationary release component 326 (e.g., toward the stationary release component 326 and away from the drug container 302). In the illustrated position, as a unit, the first compression spring 318, the spring cap 530, the flexure beam housing 320, and the clutch lock 322 can be spaced a distance 602 from the release component 326. The first compression spring 318, the spring cap 530, the flexure beam housing 320, and the clutch lock 322 can be coupled to the plunger 504 which, when the drug container 302 is empty, can be positioned closer to a far end of the drug container 302 (e.g., away from the release component 326).

The distance 602 can represent a stroke provided by the drug delivery device 100. The stroke can be considered to be the distance the plunger 504 moves when the plunger 504 fully expels the liquid drug or other agent from the drug container 302. Accordingly, this stroke distance 602 can represent the amount of movement of the plunger 504 when all of the liquid drug or other agent is provided to the patient in a single bolus (e.g., when completely filled).

Figure 7:
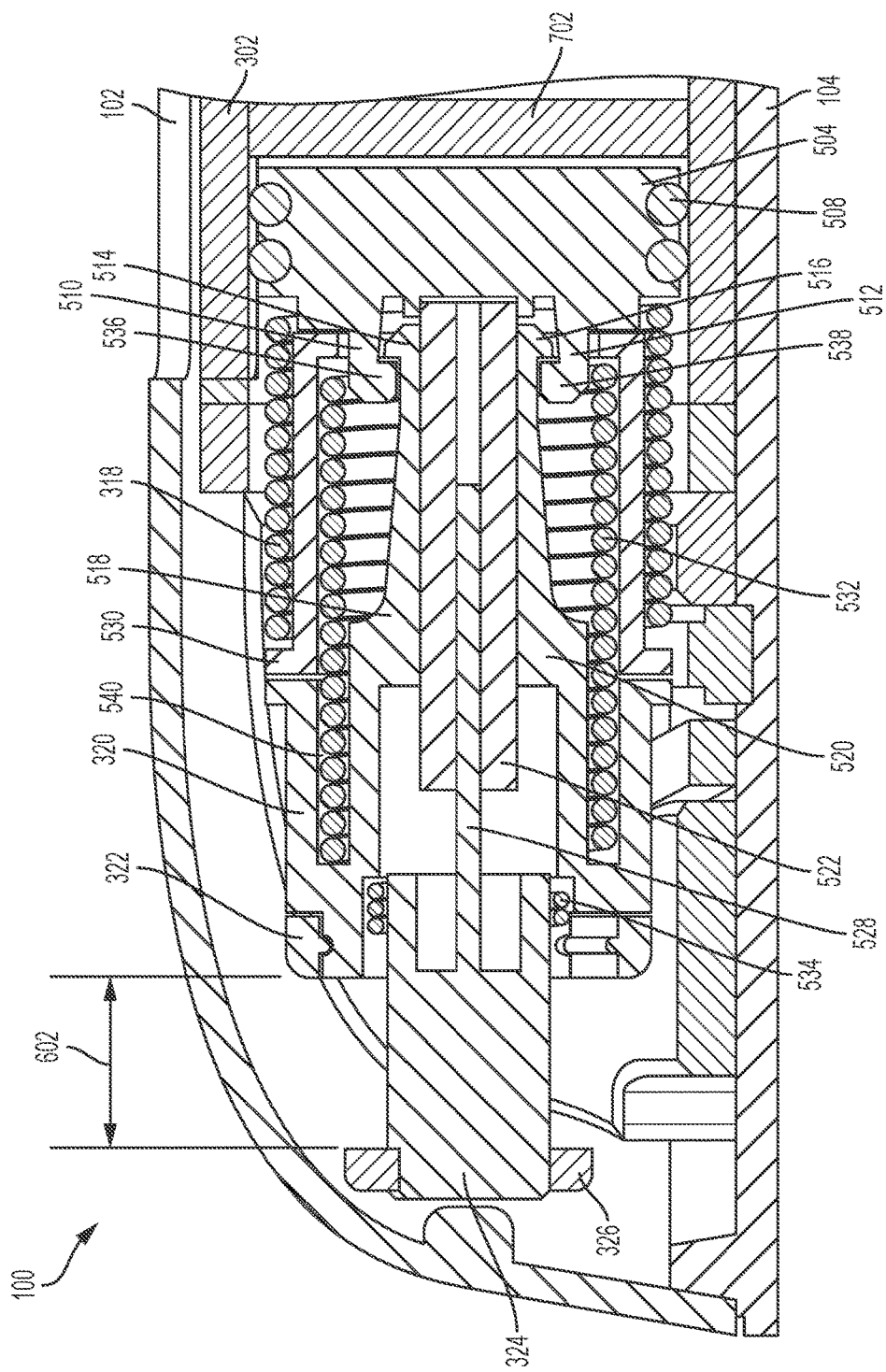
FIG. 7 illustrates a second cross-sectional view of a portion of the drug delivery device depicted in FIG. 1.

FIG. 7 illustrates a cross-sectional side view of the drug delivery device 100 corresponding to the overhead view of the drug delivery device 100 depicted in FIG. 6. FIG. 7 shows relative positioning of the components of the drug delivery device 100 in an initial state (e.g., prior to being filled with any liquid drug or other agent).

As shown in FIG. 7, the back of the flexure beam housing 320 is spaced from the release component 326 by the distance or stroke distance 602. The plunger 504 is positioned against a far wall or end wall 702 of the drug container 302 that defines an end of the reservoir 502. In the initial state of operation of the drug delivery device 100 as depicted in FIG. 7, there is no liquid drug or other agent positioned between the plunger 504 and the end wall 702 of the drug container 302 (e.g., such that the reservoir 502 does not hold or contain any liquid drug or other agent).

As further shown in FIG. 7, the release coupler 522 is coupled to the plunger 504 and is extended from the base of the fixed thrust component 324. The plunger 504 is attached to the flexure beam housing 520 by the interaction of the first depending tab 526 of the first arm 510 with the first plunger latch 514 and the interaction of the second depending tab 538 of the second arm 512 with the second plunger latch 516. The fixed thrust component 324 remains fixed in the position as shown in FIG. 7. The fixed thrust component 324 can be restricted from moving in a longitudinal direction with respect to the orientation of the drug delivery device 100 as depicted in FIG. 7 (e.g., in an axial direction). The fixed thrust component 324 can be allowed to rotate about a central axis (e.g., a central longitudinal axis) as described herein.

Figure 8:
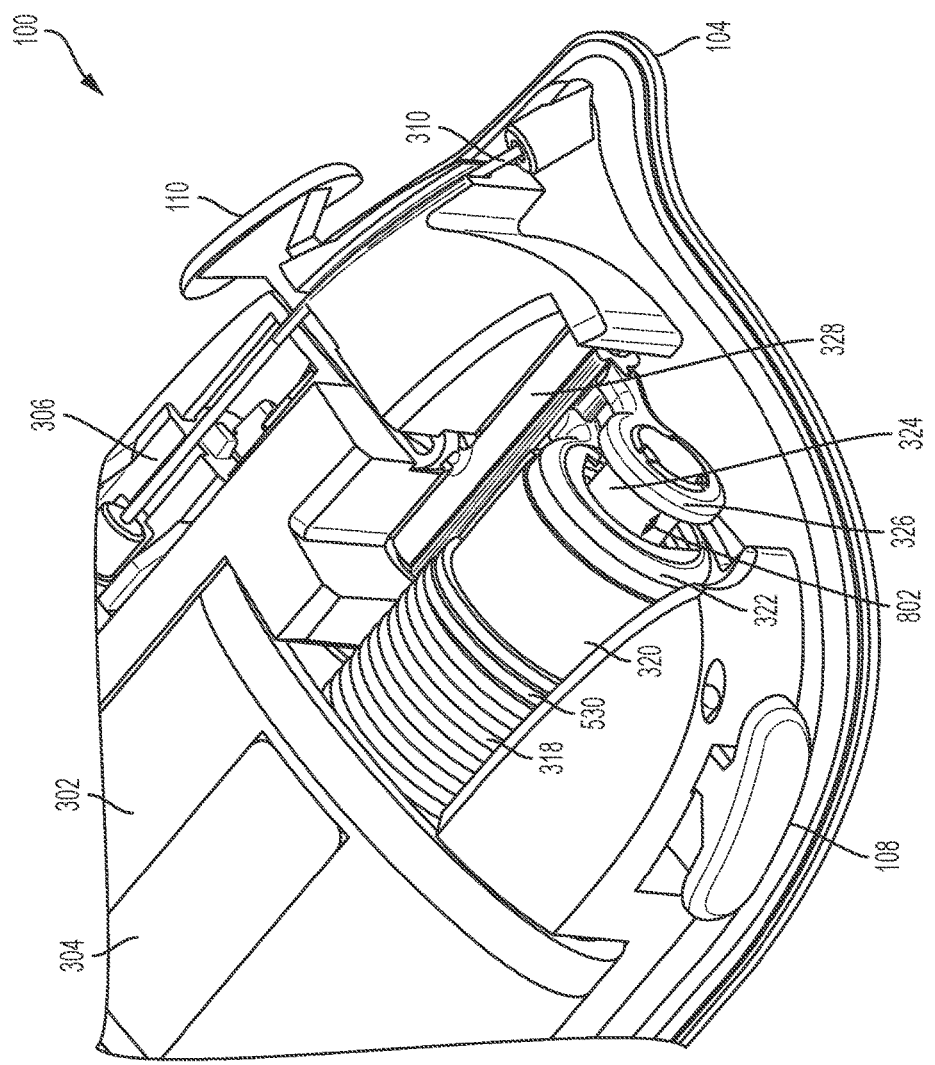
FIG. 8 illustrates a second overhead isometric view of a portion of the drug delivery device depicted in FIG. 1.

FIG. 8 illustrates a second overhead or top view of the drug delivery device 100 without the top housing component 102. FIG. 8 shows the internal components of the drug delivery device 100 as the drug container 302 is being filled with a liquid drug or other agent (e.g., such that the reservoir 502 contains a portion of a full amount of liquid drug or other agent to be stored in the reservoir 502). As shown in FIG. 8, the first compression spring 318, the spring cap 530, the flexure beam housing 320, and the clutch lock 322, as unit, are spaced a distance 802 from the release component 326. The distance 802 is less than the distance 602 (shown in FIG. 6) by an amount equal to a distance moved by the plunger 504 from the wall 702 in response to the liquid drug or other agent filling the reservoir 302.

As the reservoir 502 of the drug delivery device 100 is being filled, the plunger 504 moves in a direction opposite to the direction 506 indicated in FIG. 5 (e.g., the plunger 504 moves toward the release component 326). As a result, the first compression spring 318, the spring cap 530, the flexure beam housing 320, and the clutch lock 322 move by the same amount toward the release component 326. Accordingly, FIG. 8 shows the drug delivery device 100 in an intermediate filling state—that is, in a filling state where some amount of liquid drug or other agent has been placed into the reservoir 502.

Figure 9:
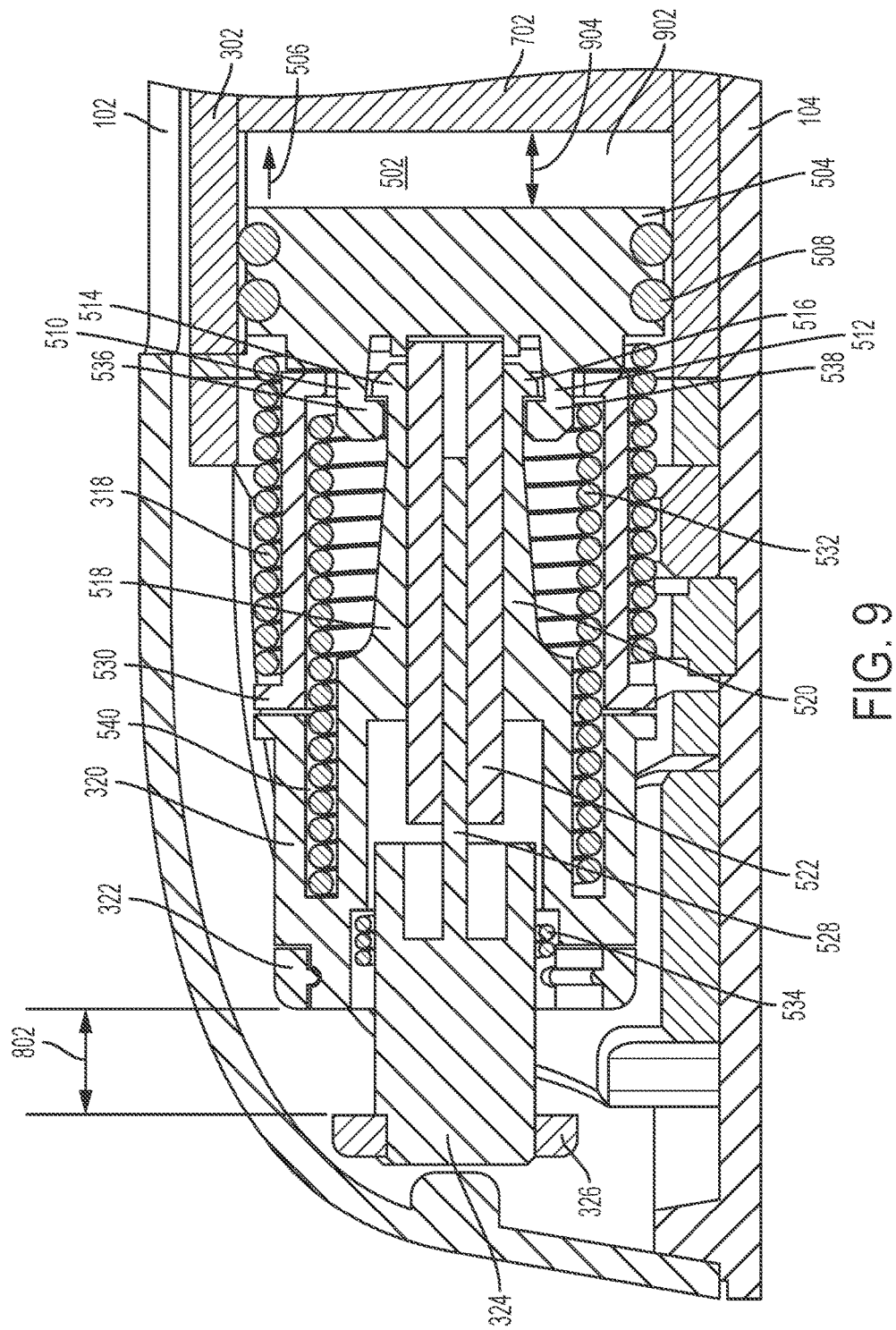
FIG. 9 illustrates a third cross-sectional view of a portion of the drug delivery device depicted in FIG. 1.

FIG. 9 illustrates a cross-sectional side view of the drug delivery device 100 corresponding to the overhead view of the drug delivery device 100 depicted in FIG. 8. FIG. 9 shows relative positioning of the components of the drug delivery device 100 in an intermediate state (e.g., when some liquid drug or other agent is being distributed into the drug delivery device 100).

As shown in FIG. 9, the back of the flexure beam housing 320 is spaced from the release component 326 by the distance 802. The plunger 504 is spaced a distance 904 from the wall 702 of the drug container 302. The distance 904 can correspond to the amount of distance the plunger 504 has moved as a result of the reservoir 502 being filled with a liquid drug or other agent 902. As shown in FIG. 9, the liquid drug or agent 902 is positioned between the plunger 504 and the end wall 702 of the drug container 302. Accordingly, in the intermediate state of filling the drug delivery device 100 as shown in FIG. 9, some amount of the liquid drug or agent 902 is contained within the reservoir 502.

As further shown in FIG. 9, the release coupler 522 remains coupled to the plunger 504 and is still extended from the base of the fixed thrust component 324. The plunger 504 remains coupled to the flexure beam housing 520 by the interaction of the first depending tab 536 of the first arm 510 with the first plunger latch 514 and the interaction of the second depending tab 538 of the second arm 512 and the second plunger latch 516. As the plunger 504 moves towards the release component 326 as the reservoir 502 is being filled, the plunger 504 can push on the spring cap 530 to move the spring cap 530 toward the release component 326. The spring cap 530 can also push on the flexure beam housing 320 to move the flexure beam housing 320 toward the release component 326. The plunger 504 can also push on the first compression spring 318.

Figure 10:
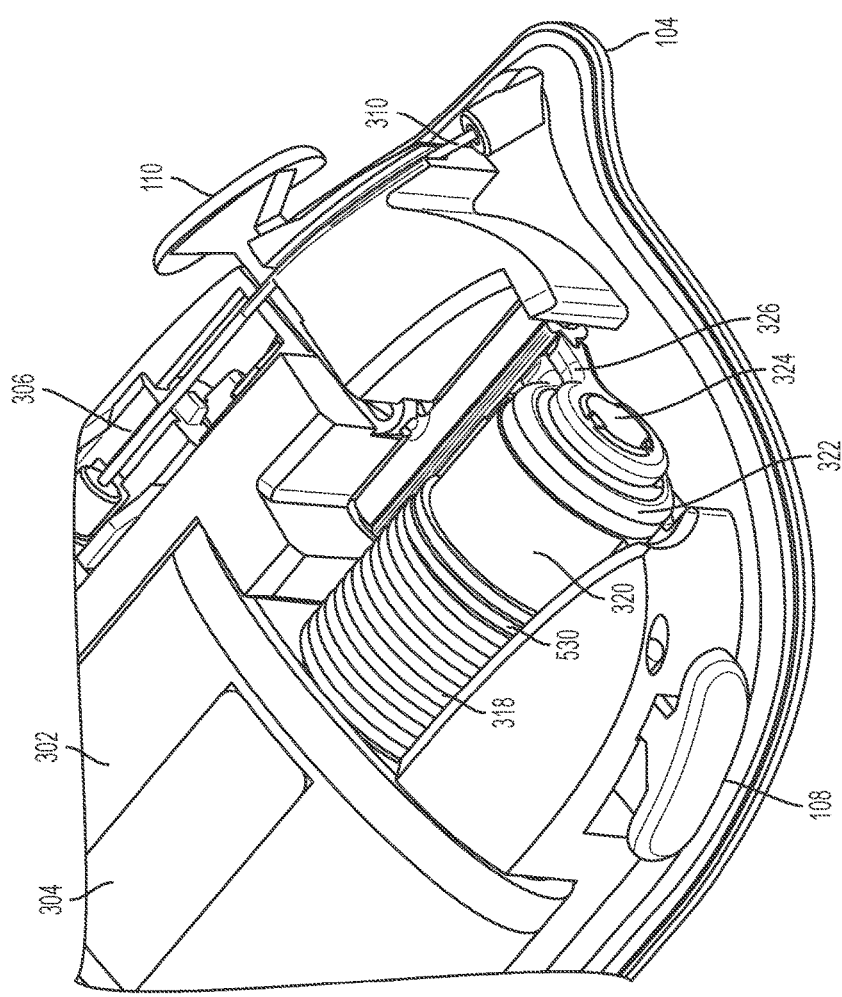
FIG. 10 illustrates a third overhead isometric view of a portion of the drug delivery device depicted in FIG. 1.

FIG. 10 illustrates a third overhead or top view of the drug delivery device 100 without the top housing 102. FIG. 10 shows the internal components of the drug delivery device 100 when the drug container 302 has been filled with the liquid drug or other agent 902 (e.g., when the reservoir 502 has been completely filled to a maximum amount). As shown in FIG. 10, the first compression spring 318, the spring cap 530, the flexure beam housing 320, and the clutch lock 322 are adjacent to, and can be in contact with, the release component 326. FIG. 10 can show the drug delivery device 100 in a completed filling state—that is, in a state where the reservoir 502 has been filled (e.g., substantially completely filled) with the liquid drug or other agent 902.

Figure 11:
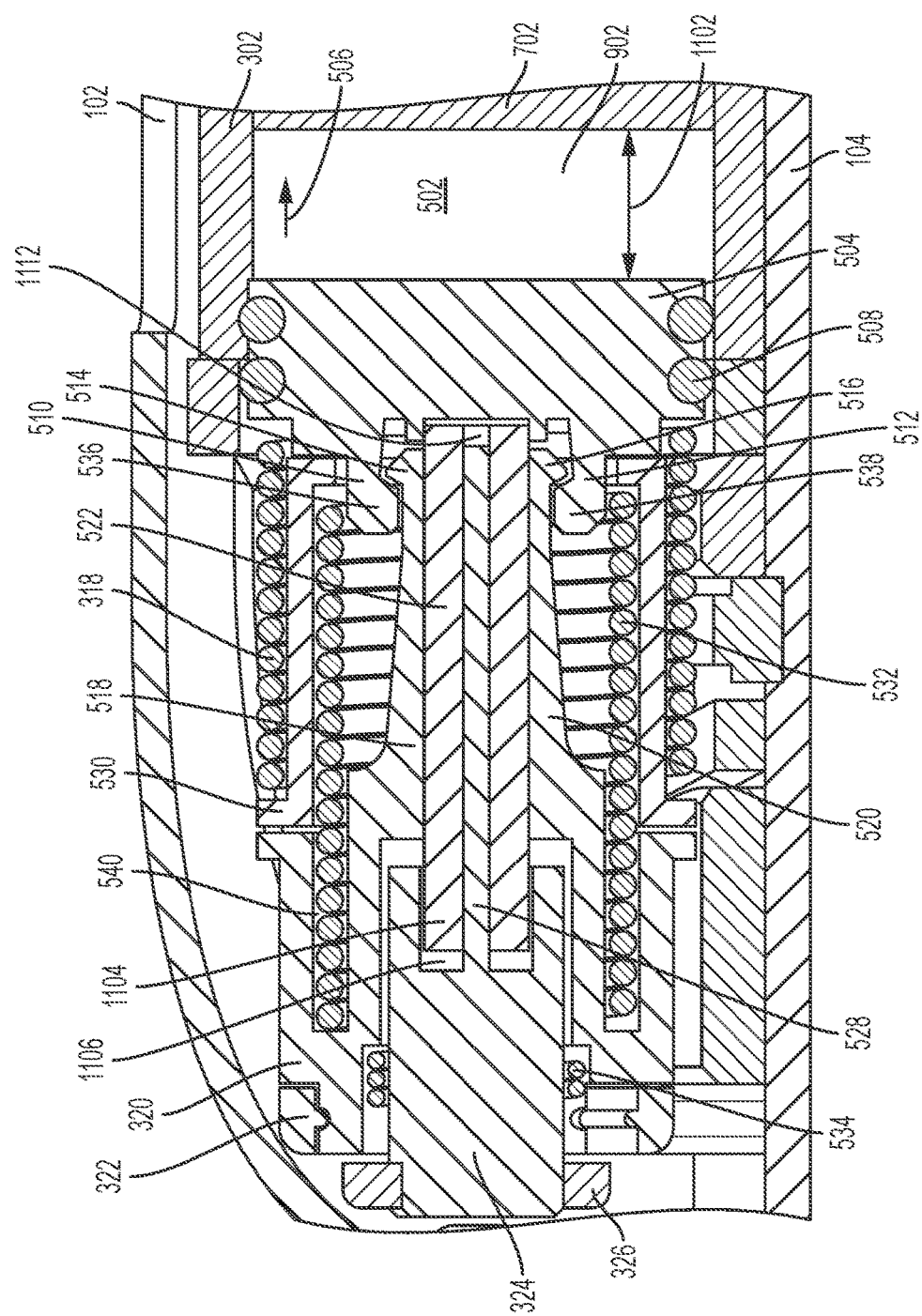
FIG. 11 illustrates a fourth cross-sectional view of a portion of the drug delivery device depicted in FIG. 1.

FIG. 11 illustrates a cross-sectional side view of the drug delivery device 100 corresponding to the overhead view of the drug delivery device 100 depicted in FIG. 10. FIG. 11 shows relative positioning of the components of the drug delivery device 100 in a filled state (e.g., when the reservoir 502 has been filled with the liquid drug or other agent 902).

As shown in FIG. 11, the back of the flexure beam housing 320 is adjacent to the release component 326. The plunger 504 is spaced a distance 1102 from the wall 702 of the drug container 302. The distance 1102 can be larger than the distance 904 depicted in FIG. 9. The distance 1102 can correspond to the amount of distance the plunger 504 has moved as a result of the reservoir 502 being filled by the liquid drug or other agent 902. The distance 1102 can correspond to the stroke distance 602 depicted in FIG. 6. As shown in FIG. 11, the liquid drug or agent 902 is positioned between the plunger 504 and the end wall 702 of the drug container 302. In the filled state of the drug delivery device 100 as shown in FIG. 11, a full dose of the liquid drug or agent 902 can be contained within the reservoir 502.

As further shown in FIG. 11, the release coupler 522 remains coupled to the plunger 504 but is adjacent to the base of the fixed thrust component 324. In particular, a first end 1104 of the release coupler 522 is positioned within an opening or pocket 1106 of the fixed thrust component 324. A second end 1112 of the release coupler 522 is adjacent to an end of the spline shaft 528 of the fixed thrust member 324. Additionally, the plunger 504 remains coupled to the flexure beam housing 520 by the interaction of the first arm 510 with the first plunger latch 514 and the interaction of the second arm 512 and the second plunger latch 516. As shown in FIG. 11, the drug delivery device 100 is in a filled state prior to activation. Accordingly, FIG. 11 can represent the drug delivery device 100 when attached to the patient prior to activation.

The clutch spring 534 can be coupled to the flexure beam housing 320. Once the reservoir 502 is filled with the liquid drug or other agent 902, the clutch spring 534 (which, as mentioned may be a torsion spring) can attach to the fixed thrust member 324 to lock the flexure beam housing 320 to the fixed thrust member 324. In various embodiments, the clutch spring 534 can attach to the fixed thrust member 324 as an initial operation after activation. For example, when the patient engages the first user interaction feature 108 and/or the second user interaction feature 110 after the reservoir 502 has been filled, the clutch spring 534 can be caused to lock the flexure beam housing 320 to the fixed thrust member 324. In various embodiments, the clutch spring 534 can be caused to lock the flexure beam housing 320 to the fixed thrust member 324 after an on-body interlock (discussed further herein) has been engaged.

The clutch spring 534 can allow a patient to load or fill the drug delivery device 100 with a user-selectable amount of the liquid drug or other agent 902. The user-selectable amount can be approximately a total fixed amount the drug delivery device 100 can hold or can be an amount less than the total fixed amount the drug delivery device 100 is capable of holding. Locking the clutch spring 534 to the fixed thrust member 324 can establish an initial starting point or first position of the plunger 504 from which the plunger 504 can later be moved (e.g., to an end position or a second position) that expels the liquid drug or other agent from the drug delivery device 100. The clutch sprint 534 can couple the flexure beam housing 320 to the fixed thrust member 324 along any portion of the base of the fixed thrust member 324 based on the amount of liquid drug or other agent placed into the reservoir 502.

Figure 12:
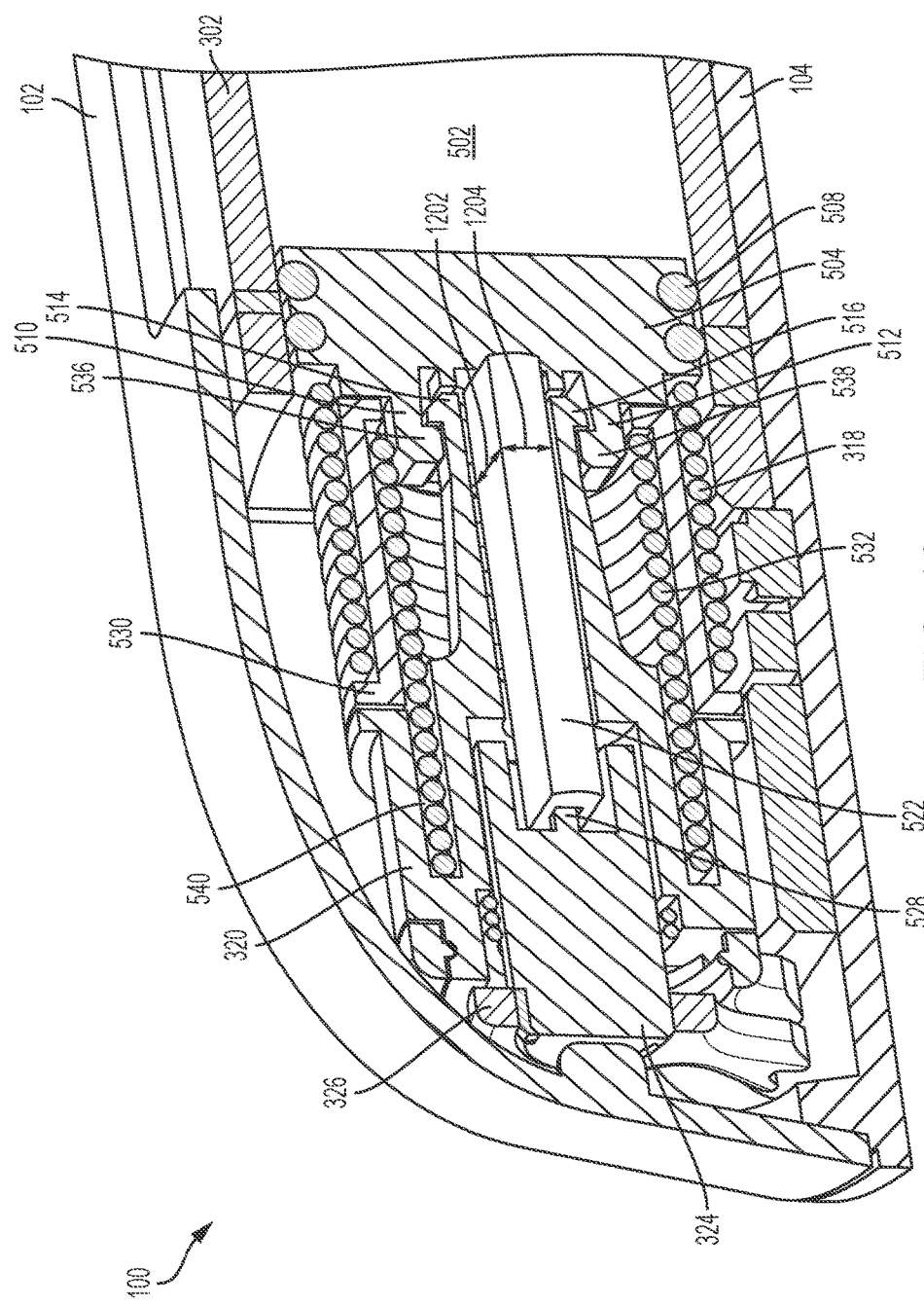
FIG. 12 illustrates a fifth cross-sectional view of a portion of the drug delivery device depicted in FIG. 1.

FIG. 12 illustrates the drug delivery device 100 after activation. In particular, FIG. 12 provides a cross-sectional view of the drug delivery device 100 to show the initial operation of the internal components of the drug delivery device 100 once activated.

In various embodiments, when the drug delivery device 100 is initially activated, the fixed thrust component 324 can be caused to rotate. The fixed thrust component 324 can rotate about a central longitudinal axis of the fixed thrust member 324. The fixed thrust component 324 can be rotated by a few degrees in either direction relative to the central longitudinal axis of the fixed thrust component 324. The release coupler 522, which is coupled to the fixed thrust component 324 (e.g., the release coupler 522 and the spline shaft 528 of the fixed thrust component 324 can be splined together), can also rotate in response to the rotation of the fixed thrust member 324.

The release coupler 522 can have a non-circular cross-sectional shape (e.g., square shaped, diamond shape, polygon shaped) such that the release coupler 522 has a thickness in a vertical direction (e.g., relative to the orientation of the release coupler 522 as shown in FIG. 12) prior to rotation that is larger than a thickness of the release coupler 522 after rotation. This feature of the release coupler 522 can be seen in FIG. 12 wherein a vertical thickness of the release coupler 522 after rotation is less than a vertical thickness of the release rod prior to rotation (e.g., compare vertical thickness of the release rod as depicted in FIG. 5 to the vertical thickness of the release coupler 522 as depicted in FIG. 12).

As an example, a first thickness 1202 of the release coupler 522 can be thicker than a second thickness 1204 of the release coupler 522. The first thickness 1202 can represent a thickness of the release coupler 522 in a first direction. The second thickness 1204 can represent a thickness of the release coupler 522 in a second direction (e.g., orthogonal to the first direction). With reference to the orientation of the release coupler 522 as shown in FIG. 12, prior to activation, the release coupler 522 can be orientated such that the first thickness 1202 is oriented vertically and the second thickness 1204 is oriented horizontally. After activation, the release coupler 522 can rotate about an axis such that the first thickness 1202 is oriented horizontally and the second thickness 1204 is oriented vertically (as depicted in FIG. 12). This difference in the first and second thicknesses 1202 and 1204 of the release coupler 522, and the rotation of the release coupler 522, can trigger release of the plunger 504 as described more fully herein.

In general, the release coupler 522 can have a thickness in a first direction that is larger than a thickness in a second direction, with the first and second directions being perpendicular to one another. With respect to FIG. 5, the increased thickness of the release coupler 522 prior to rotation ensures the first arm 518 and the second arm 520 are maintained apart from one another such that the plunger latch 514 is engaged with the first depending tab 536 of the first arm 510 and the second plunger latch 516 is engaged with the second depending tab 538 of the second arm 512.

Once the release coupler 522 is rotated to have a narrower vertical profile as shown in FIG. 12, the release coupler 522 no longer maintains the separation of the first and second arms 518 and 520 of the flexure beam housing 320 as shown in FIG. 5. As a result, the first and second arms 518 and 520 can be allowed to release inward. The movement of the first and second arms 518 and 520 inward allows the first plunger latch 514 and the second plunger latch 516 to disengage from the first and second depending tabs 536 and 538 of the first and second arms 510 and 512, respectively. As a result, the first plunger latch 514 can move under the first depending tab 536 and the second plunger latch 516 can move over the second depending tab 538.

The first and second arms 518 and 520 of the flexure beam housing 320 can be biased toward one another to facilitate the movement of the first plunger latch 514 under the first arm 510 and the movement of the second plunger latch 516 over the second arm 512 when the release coupler 522 is rotated. Further, the forces provided by the first and second compression springs 318 and 532, by acting on the plunger 504, can facilitate movement of the first plunger latch 514 under the first depending tab 536 and movement of the second plunger latch 516 over the second depending tab 538.

Accordingly, as a result of the fixed thrust component 324 rotating, and the release coupler 522 rotating in response thereto, the plunger 504 can be unlatched and/or disengaged from the flexure beam housing 324. The first and second depending tabs 536 and 538 and the first and second plunger latches 514 and 516 can be correspondingly shaped (e.g., ramped) to facilitate release of the first and second plunger latches 514 and 516.

Figure 13:
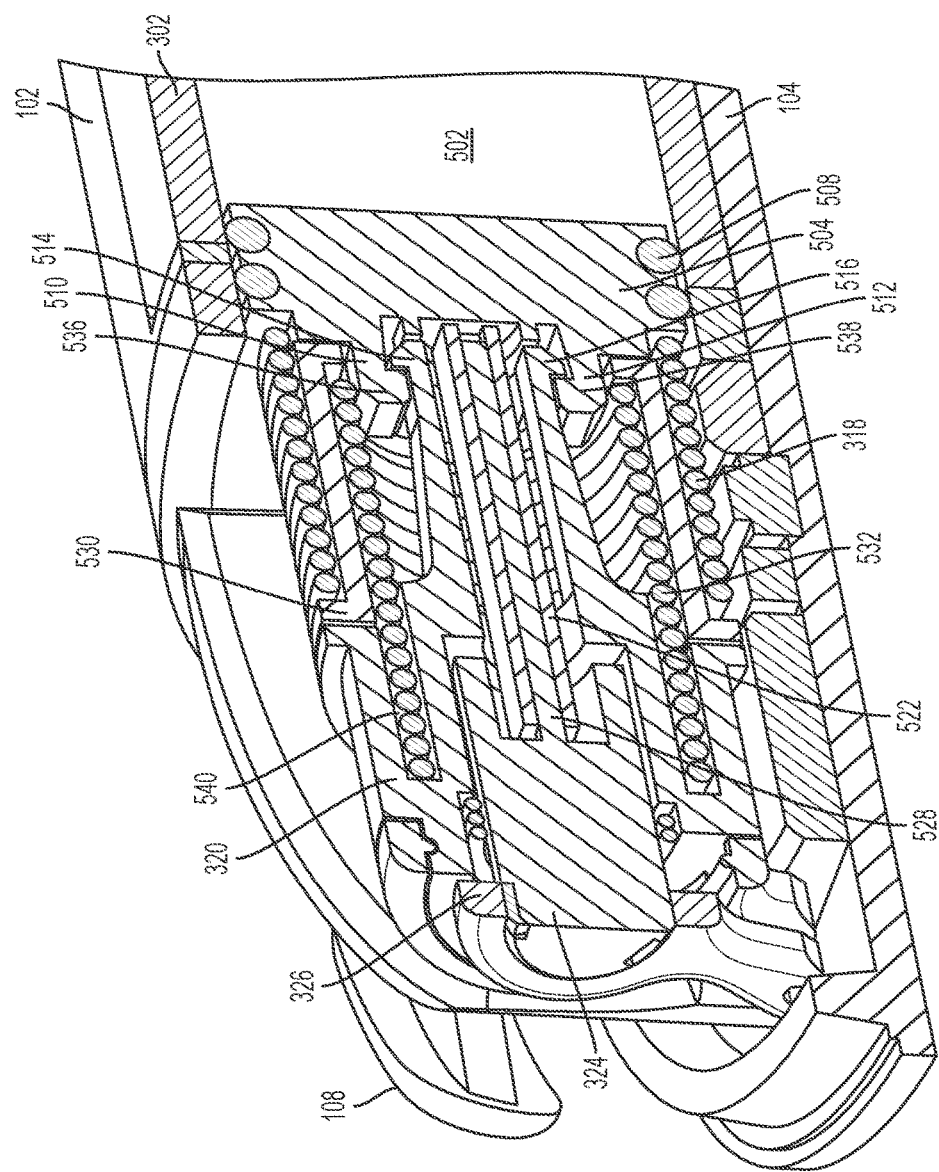
FIG. 13 illustrates a sixth cross-sectional view of a portion of the drug delivery device depicted in FIG. 1.

FIG. 13 illustrates a second view of the drug delivery device 100 as depicted in FIG. 12. FIG. 13 illustrates the release coupler 522 in cross-section. As shown in FIG. 13, the release coupler 522 no longer presses the first plunger latch 514 upwards against the first depending tab 536 of the first arm 510 and no longer presses the second plunger latch 516 downward against the second depending tab 536 of the second arm 512. In this position, the bias of the first and second compression springs 318, 532 can cause the plunger 504 to move in the direction 506 (FIG. 11), as will be described below.

FIGS. 14-16 illustrate the drug delivery device 100 in various stages of providing the liquid drug or other agent 902 to the patient. FIGS. 14-16 show the interaction of the components depicted in FIG. 5 as the reservoir 302 begins in a filled state and ends in an empty state. In particular, FIGS. 14-16 show the interaction of components that cause the plunger 504 to expel the liquid drug or other agent 902 from the reservoir 502 by moving the plunger in the direction 506.

FIG. 14 illustrates a cross-sectional view of the drug delivery device 100 as the plunger 504 is disengaged from the flexure beam housing 320. As shown in FIG. 14, the release coupler 522 has been rotated such that the first and second arms 518 and 520 of the flexure beam housing 320 move toward one another. Further, the first plunger latch 514 moves under the first depending tab 536 of the first arm 510 of the plunger 504 and the second plunger latch 516 moves over the second depending tab 538 of the second arm 512 of the plunger 504 to release (and/or decouple or disengage) the plunger 504 from the flexure beam housing 320. FIG. 14 can be considered to represent a state of the drug delivery device 100 just after activation.

FIG. 15 illustrates the operation of the drug delivery device 100 subsequent to the state of the drug delivery device 100 as depicted in FIG. 14. After the plunger 504 is disengaged from the flexure beam housing 320, movement of the first and second compression springs 318 and 532 is no longer restricted. As a result, the first and second compression springs 318 and 532 begin to expand in the direction 506. The expansion of the first and second compressions springs 318 and 532 causes the plunger 504 to move in the direction 506. The flexure beam housing 320 remains in a fixed position and does not move in the direction 506. The release coupler 522 moves with the plunger 504 in the direction 506. In general, the release coupler 522 telescopes away from the fixed thrust component 324 as the plunger 504 moves in the direction 506. As the plunger 504 moves in the direction 506, a portion of the liquid drug or agent 902 stored in the reservoir 502 is expelled and delivered to the patient via the needle conduit 308 and needle 310.

As shown in FIG. 15, the first compression spring 318 can be coupled between a first end of the spring cap 530 and the plunger 504. The first end of the spring cap 530, which can have an upwardly extending portion (or lip), can provide a base or platform for the first compression spring 318 (e.g., a push off point) to provide a force against the plunger 504. The second compression spring 532 can be coupled between an opening in the flexure beam housing 320 (e.g., the recess 540) and a second end of the spring cap 530. The flexure beam housing 320 can provide a base or platform for the second compression spring 532 to provide a force against the second end of the spring cap 320. Together, the expansion of the first and second compression springs 318 and 532 and the movement of the spring cap 320 can propel the plunger 504 in the direction 506.

FIG. 16 illustrates the operation of the drug delivery device 100 subsequent to the state of the drug delivery device 100 as depicted in FIG. 15. As shown in FIG. 16, the plunger 504 has moved further into the reservoir 502. As a result, additional portions of the liquid drug or agent 902 have been expelled from the reservoir 502 and out through the needle conduit 308 and needle 310. The first and second compression springs 318 and 532 have further expanded and have propelled the plunger 504 and the spring cap 530 in the direction 506. The operation of the internal components for the drug delivery device 100 can continue as depicted in FIGS. 14-16 until the first and second compression springs 318, 522 have fully expanded and/or when the plunger 504 reaches an end of the reservoir 502 (e.g., the end wall 702) and substantially all of the liquid drug or agent 902 stored in the reservoir 502 has been expelled. FIGS. 14-16 can therefore represent various stages of expelling the liquid drug or agent 902 from the reservoir 502 prior to the drug delivery device 100 being completely emptied.

The components of the drug delivery device 100 that interact in response to the filling of the reservoir 502 and that also interact to drive the plunger 504 to expel the stored liquid drug or other agent 904 can be considered to be an infusion engine of the drug delivery device 100. In various embodiments, the infusion engine, with reference to FIG. 5, can be considered to comprise the release component 326, the fixed thrust member 324, the release coupler 522, the clutch spring 534, the flexure beam housing 320, the spring cap 530, and/or the first and second compression springs 318 and 532.

Figure 17:
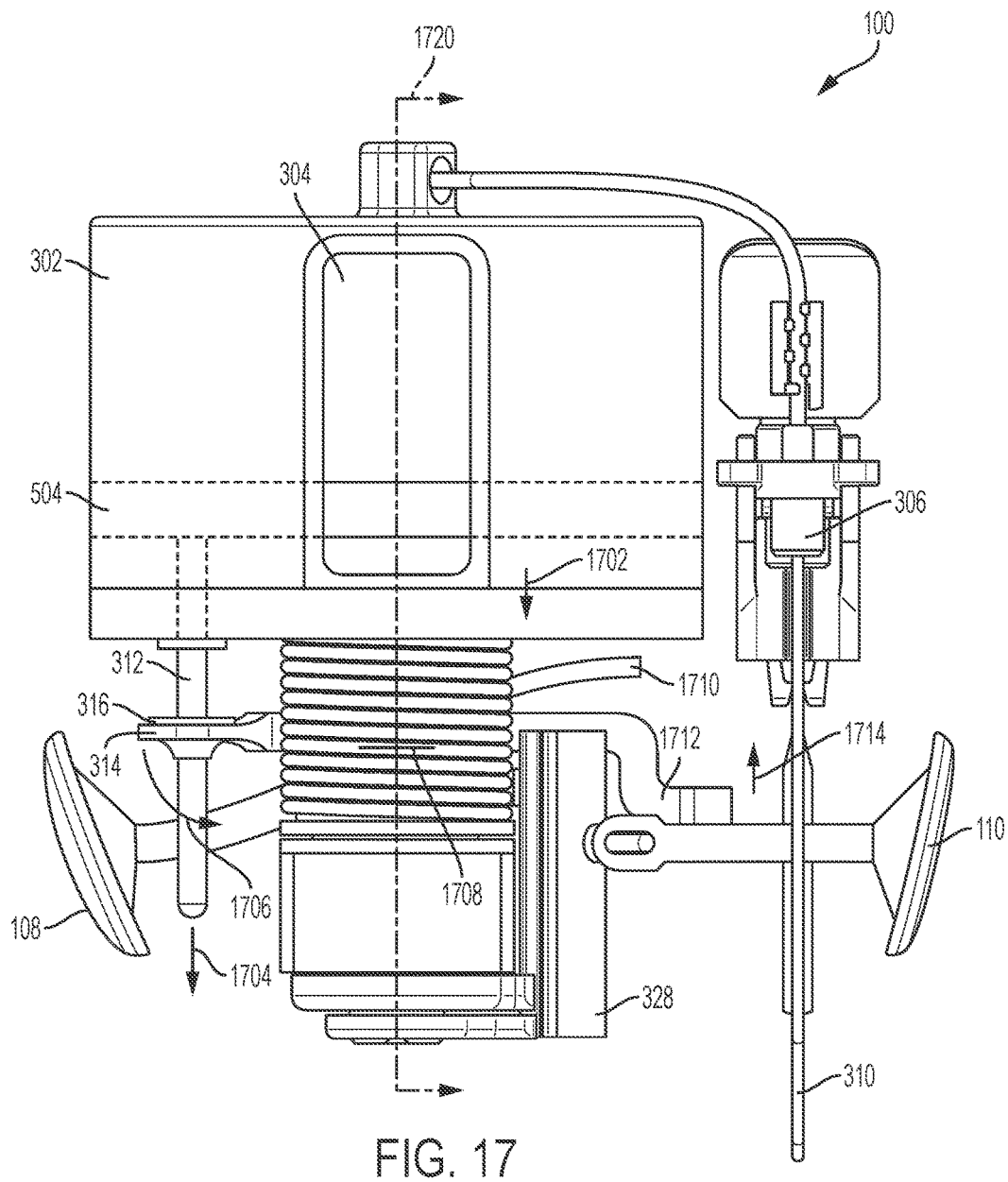
FIG. 17 illustrates an overhead view of a portion of the internal components of the drug delivery device depicted in FIG. 1.

FIGS. 17-20 illustrate exemplary operation of various internal components of the drug delivery device 100 as the drug delivery device 100 is being filled and subsequently activated. FIG. 17 illustrates an overhead view of a portion of the drug delivery device 100. In particular, FIG. 17 shows relative operation of various components of the drug delivery device 100 as the drug delivery device 100 is being filled with a liquid drug or other agent. Specifically, FIGS. 17-20 show a sequence of operational configurations in which the drug delivery device 100 can be activated using the first and second user interaction features 108 and 110. In various embodiments, the second user interaction feature 110 can remain locked (e.g., unable to move) and unable to activate the drug delivery device 100 until the first user interaction feature 108 is engaged. As will be appreciated, this arrangement may minimize or eliminate the chance that the drug delivery device 100 may be inadvertently activated.

The plunger 504 is shown positioned within the drug container 302 and can be partially visible through the window 304. The fill rod 312 is coupled to the plunger 504 and can move linearly with the plunger 504. As the drug container 302 is being filled, the plunger 504 can move in a direction 1702. Since the fill rod 312 is coupled to the plunger 504, the fill rod 312 will move in a direction 1704.

The fill rod 312 can move inside an opening in the elastomeric boot connector 316 that is coupled to the fill lever 314. The elastomeric boot connector 316 can be tightly fit around the fill rod 312 such that when the fill rod 312 moves in the direction 1704, the fill lever 314 can be caused to move. In particular, the fill lever 314 can be caused to rotate in a direction 1706 about an indicated axis 1708.

The fill lever 314 can be coupled to a first arm 1710 and a second arm 1712. An end of the second arm 1712 can be coupled to the second user interaction feature 110. In particular, the end of the second arm 1712 can be positioned within an opening or slot of the second user interaction feature 110 (not shown in FIG. 17). The movement of the fill lever 314 in the direction 1706 about the axis 1708 can cause the second arm 1712 to move in a direction 1714 away from the second user interaction feature 110. As a result, the end of the second arm 1712 can move out of the opening or slot of the second user interaction feature 110. The arrangement of the end of the second arm 1712 within the opening in the second user interaction feature 110 can be a locking feature that can be unlocked or detached during the filling process, as the fill rod 312 moves in the direction 1704.

Figure 18:
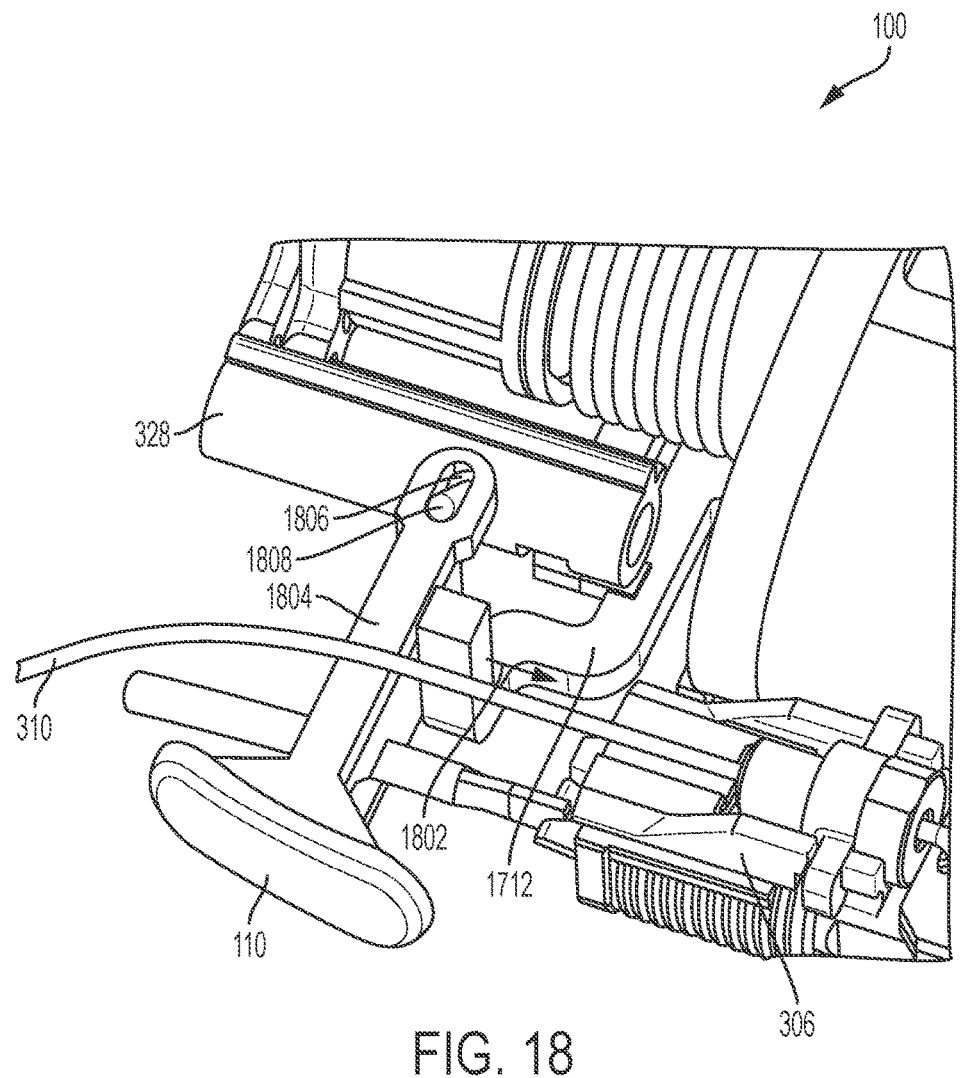
FIG. 18 illustrates a side overhead isometric view of a portion of the internal components of the drug delivery device depicted in FIG. 17.

FIG. 18 illustrates a second view of the drug delivery device 100 as depicted in FIG. 17. As shown in FIG. 18, the second user interaction feature 110 includes an arm or extension 1804. The extension 1804 includes an opening 1806 positioned at an end of the extension 1804 in proximity to the tube gear 328. An extension 1808 of the tube gear 328 can extend from the tube gear 328 and can be positioned within the opening 1806.

FIG. 18 furthers shows a direction 1802 (corresponding to the direction 1714) that the second arm 1712 moves when the fill lever 314 moves in the direction 1706 as shown in FIG. 17. A portion of the second arm 1712 can be positioned within an opening or slot of the arm 1804. When the second arm 1712 moves in the direction 1802, the end portion of the second arm 1712 can move out of the opening in the extension 1804.

Figure 19:
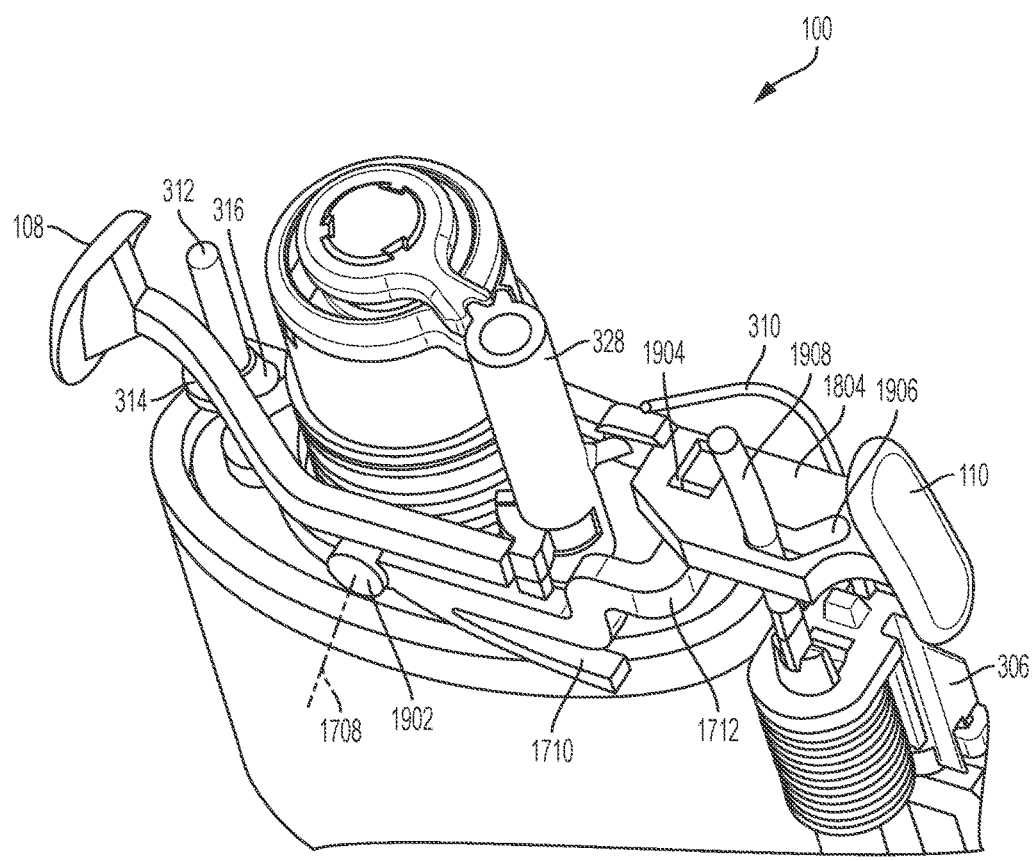
FIG. 19 illustrates a rear underside isometric view of a portion of the internal components of the drug delivery device depicted in FIG. 17.

FIG. 19 illustrates a third view of the drug delivery device 100 as depicted in FIG. 17. As shown in FIG. 19, the fill lever 314 is coupled to the first and second arms 1710 and 1712. The axis 1708 about which the fill lever 314 rotates is shown to intersect a point of rotation 1902. The arm 1804 of the second user interaction feature 110 is shown to include a first opening 1904 in which the end of the second arm 1712 is inserted.

The arm 1804 can further include a second opening or slot 1906. A release bar 1908 of the needle insertion component 306 is positioned through the opening 1906. As shown in FIG. 19, when the end of the second arm 1712 is positioned within the first opening 1904, the second user interaction feature 110 can be considered to be locked. When the end of the second arm 1712 is removed from the first opening 1904, the second user interaction feature 110 can be considered to be unlocked. Lateral movement of the second user interaction feature 110 (and the arm 1804) can still be further restricted by the tube gear 328 however as will be described further in relation to FIG. 20.

FIG. 19 further shows that as the fill lever 314 rotates about the axis 1708, the end of the second arm 1712 can move out of the first opening 1904 to unlock the second user interaction feature 110. This unlocking of the second user interaction feature 110 can occur as the drug delivery device 100 is being filled and can be initiated by movement of the plunger 504 and therefore movement of the fill rod 312 in the direction 1704 as depicted in FIG. 17.

After the end of the second arm 1712 is no longer positioned within the first opening 1904, the second user interaction feature 110 can be considered to be unlocked. However, as described above, the second user interaction feature 110 can be prevented from moving (e.g., laterally) until the first user interaction feature 108 is engaged.

Figure 20:
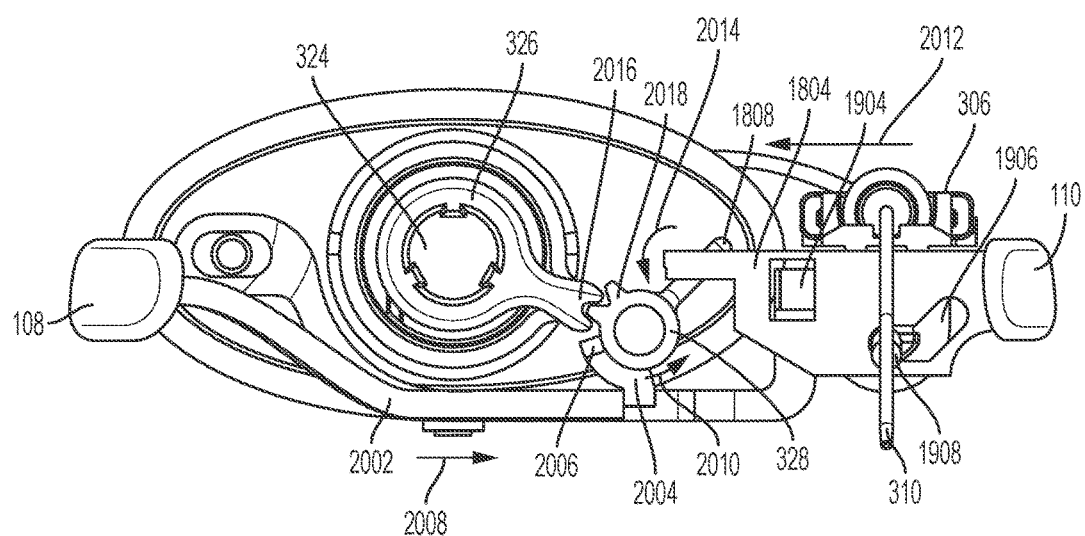
FIG. 20 illustrates a rear view of a portion of the internal components of the drug delivery device depicted in FIG. 17.

FIG. 20 illustrates a fourth view of the drug delivery device 100 as depicted in FIG. 17. As shown in FIG. 20, the first user interaction feature 108 can be coupled to an arm 2002. An end of the arm 2002 can be adjacent to and/or coupled to a dead bolt component 2004. The deadbolt component 2004 can prevent the tube gear 328 from rotating (e.g., in a counterclockwise direction relative to the depiction of the drug delivery device 100 in FIG. 20). Specifically, the deadbolt component 2004 can be adjacent to and/or coupled to an extension 2006 of the tube gear 328. The tube gear 328 can be prevented from rotating due to the extension 2006 being unable to rotate with the deadbolt feature 2004 blocking a direction of rotation.

When the first user interaction feature 108 is engaged and/or manipulated, the arm 2002 can push on the deadbolt feature 2004 by moving in a direction 2008. The deadbolt feature 2004 can then be moved and can be rotated in a direction 2010. When the deadbolt feature 2004 is rotated in the direction 2010, the deadbolt feature 2004 can be moved so as to no longer prevent movement of the tube gear 328 since the extension 2006 is no longer blocked from rotating by the deadbolt feature 2004.

When rotation of the tube gear 328 is no longer prevented by the deadbolt feature 2004, the second user interaction feature 110 and the arm 1904 can be moved laterally. Specifically, the second user interaction feature 110 can be engaged and/or manipulated by a user to move in a direction 2012.

Manipulation of the second user interaction feature 110 after rotation of the tube gear 328 is unlocked can initiate two actions. First, the release bar 1908 coupled to the needle insertion component 306 can be caused to move in the upper region of the slot 1906. This movement of the release bar 310 can trigger the needle insertion component 306. Triggering the needle insertion component 306 can cause the end of the needle 310 to be inserted into the patient. Second, the extension 1808 can be caused to move and/or rotate in a direction 2014. Movement of the extension 1808 in the direction 2014 causes the tube gear 328 to rotate in the same direction 2014. The tube gear 328 is free to rotate since prior engagement of the first user interaction feature 108 resulted in the deadbolt feature 2004 moving so as to no longer block movement of the extension 2006.

Further, the tube gear 328 can be coupled to the release component 326. As an example, an extension prong 2016 of the release component 326 can be coupled to an extension prong 2018 of the tube gear 328. Accordingly, when the tube gear 328 rotates in the direction 2014, the release component 326 can be caused to rotate. As shown in FIG. 20, the release component 326 can be rotated in a direction opposite to the counterclockwise direction 2014.

As further shown in FIG. 20, the release component 326 is coupled to the fixed thrust component 324. Rotation of the fixed thrust component 324 rotates the release coupler 522, thereby initiating advancement of the plunger 504 to expel the liquid drug or other agent from the drug container 302 as discussed in relation to FIGS. 12-16.

In various embodiments, the drug delivery device 100 can be implemented as a fully mechanical system. In various embodiments, the infusion engine of the drug delivery device 100 can be implemented as a fully mechanical system.

In various embodiments, the second user interaction feature 110 can remain locked (e.g., unable to move in the direction 2012) and unable to activate the drug delivery device 100 until the first user interaction feature 108 is engaged. The two step process for activating the drug delivery device 100—requiring engagement of the first and second user interaction features 108 and 110 either sequentially or approximately simultaneously—provides a safety feature and prevents erroneous or unintended activation of the drug delivery device 100.

In various embodiments, the mechanisms for activating the drug delivery device 100 after it has been filled with a liquid drug or other agent can be mechanical systems as explained in relation to FIG. 20. In various alternative embodiments, the drug delivery device 100 can include an on-body interlock. The on-body interlock can be implemented in lieu of the first user interaction feature 108. That is, the on-body interlock can replace the functions and operation of the first user interaction feature 108. When the drug delivery device 100 is implemented with an on-body interlock, the on-body interlock can be engaged by the drug delivery device being placed onto a patient. Prior to placing the drug delivery device 100 onto the patient, the drug delivery device 100 cannot be activated. The on-body interlock can include an extension that projects from the drug delivery device 100—for example, from an outer surface of the lower housing component 104—that can be triggered or moved in response to being coupled to the patient. Once triggered, the on-body interlock can allow manipulation of the second user interaction feature 110. The drug delivery device 100 can include a single user interaction feature when implemented with the on-body interlock feature.

Figure 21:
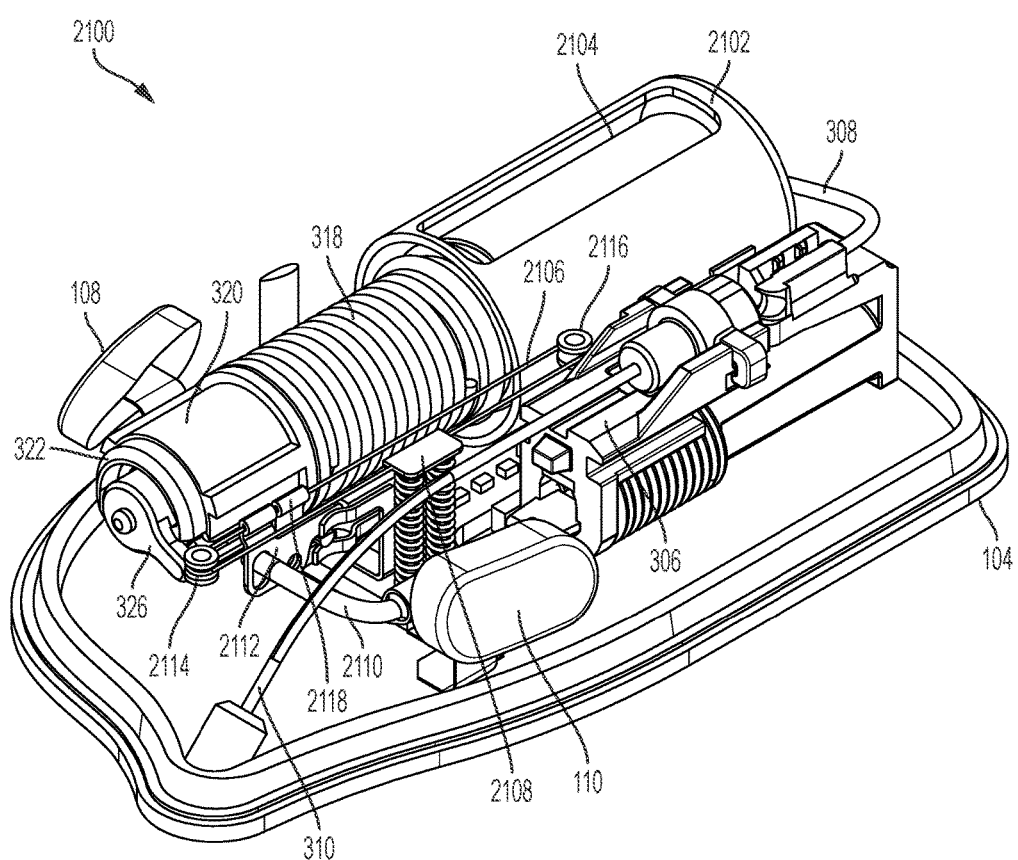
FIG. 21 illustrates an isometric view of a second exemplary embodiment of a variable fill drug delivery device.

FIG. 21 illustrates a variable fill drug delivery device 2100. The drug delivery device 2100 can include many of the same or substantially similar components as the drug delivery device 100 and can be operated to deliver a stored liquid drug or other agent to a patient in a substantially similar manner to the operation of the drug delivery device 100. Accordingly, in the following description of the drug delivery device 2100, reference may be made to components described in relation to the drug delivery device 100 where the drug delivery device 2100 includes or uses the same component or a substantially similar component. In various embodiments, the drug delivery device 2100 can include an infusion engine that includes substantially the same components and operates in a substantial same manner as described in relation to the drug delivery device 100. In various embodiments, the drug delivery device 2100 may include one or more electromechanical components or features for activating the drug delivery device 2100. In various embodiments, the drug delivery device 2100 can differ from the drug delivery device 100 by mechanisms and/or components for activating the drug delivery device 100 as explained further herein.

As shown in FIG. 21, the drug delivery device 2100 can include a drug container 2102. The drug container 2102 can have a different size and shape than the drug container 302 but can otherwise be substantially the same and operate in a substantially similar manner to the drug container 302. The drug container 2102 can also include a window 2104 similar to the window 304. The smaller sized drug container 2102 allows the drug delivery device 2100 to have an overall smaller shape and form factor than the drug delivery device 100 but is not so limited. Any sized and shaped drug container 2102 and corresponding plunger can be used with either the drug delivery device 100 or the drug delivery device 2100.

The drug delivery device 2100 can include a shape-memory alloy (SMA) wire 2106. The SMA wire 2106 can be coupled to an electrical power source (not shown in FIG. 21) by way of a contact 2108, a first pole or connector 2114, and a second pole or connector 2116. The power source can be, for example, a battery or a capacitor. The power source can be used to energize two sides of the SMA wire 2106 as further described herein. The first connector 2114 can be coupled to a first output of the power source (e.g., a positive output terminal of the power source) and the second connector 2116 can be coupled to a second output of the power source (e.g., a negative output terminal of the power source). The contact 2108 can be connected to ground or a ground terminal.

The user interaction features 108 and 110 can be coupled electrically to a printed circuit board assembly (PCBA) by, for example, flex cables or other wires. The SMA wire 2106 can be energized to pull and release stored energy elements as further described herein.

As shown in FIG. 21, the drug delivery device 2100 can include a release bar 2110. The release bar 2110 can be coupled to the needle insertion component 306. When moved in a predetermined manner or direction, the release bar 2110 can activate the needle insertion component 306. As a result, a tip or end of the needle 310 can be inserted into the patient.

The drug delivery device 2100 can further include a release lever 2112. The release lever 2112 can be coupled to the release bar 2110. The release lever 2112 can be electrically coupled to the contact 2108. The portion of the SMA wire 2106 between the first connector 2114 and the release lever 2112 can be energized to contract or change shape. When this portion of the SMA wire 2106 is energized, the release lever 2112 can cause the release bar 2110 to move in a predetermined direction that causes the needle insertion component 306 to activate.

The drug delivery device 2100 can also include a release lever 2118. The release lever 2118 can be coupled to a release bar (not shown in FIG. 21) that can initiate movement of the plunger 504. In various embodiments, the release bar can be coupled to the release component 326. The release lever 2118 can be electrically coupled to the contact 2108. The portion of the SMA wire 2106 between the second connector 2116 and the release lever 2118 can be energized to contract or change shape. When this portion of the SMA wire 2106 is energized, the release lever 2118 can cause the release bar to move in a predetermined direction that triggers the plunger 504 to begin to expel the stored liquid drug or agent 902. In various embodiments, the release lever 2118 can restrict the release bar from rotating prior to the portion of the SMA wire 2106 between the second connector 2116 and the release lever 2118 being energized. Accordingly, energizing the SMA wire 2106 between the second connector 2116 and the release lever 2118 can cause the release lever 2118 to move so as to no longer restrict movement of the release bar, allowing movement of the plunger 504 to begin.

Figure 22:
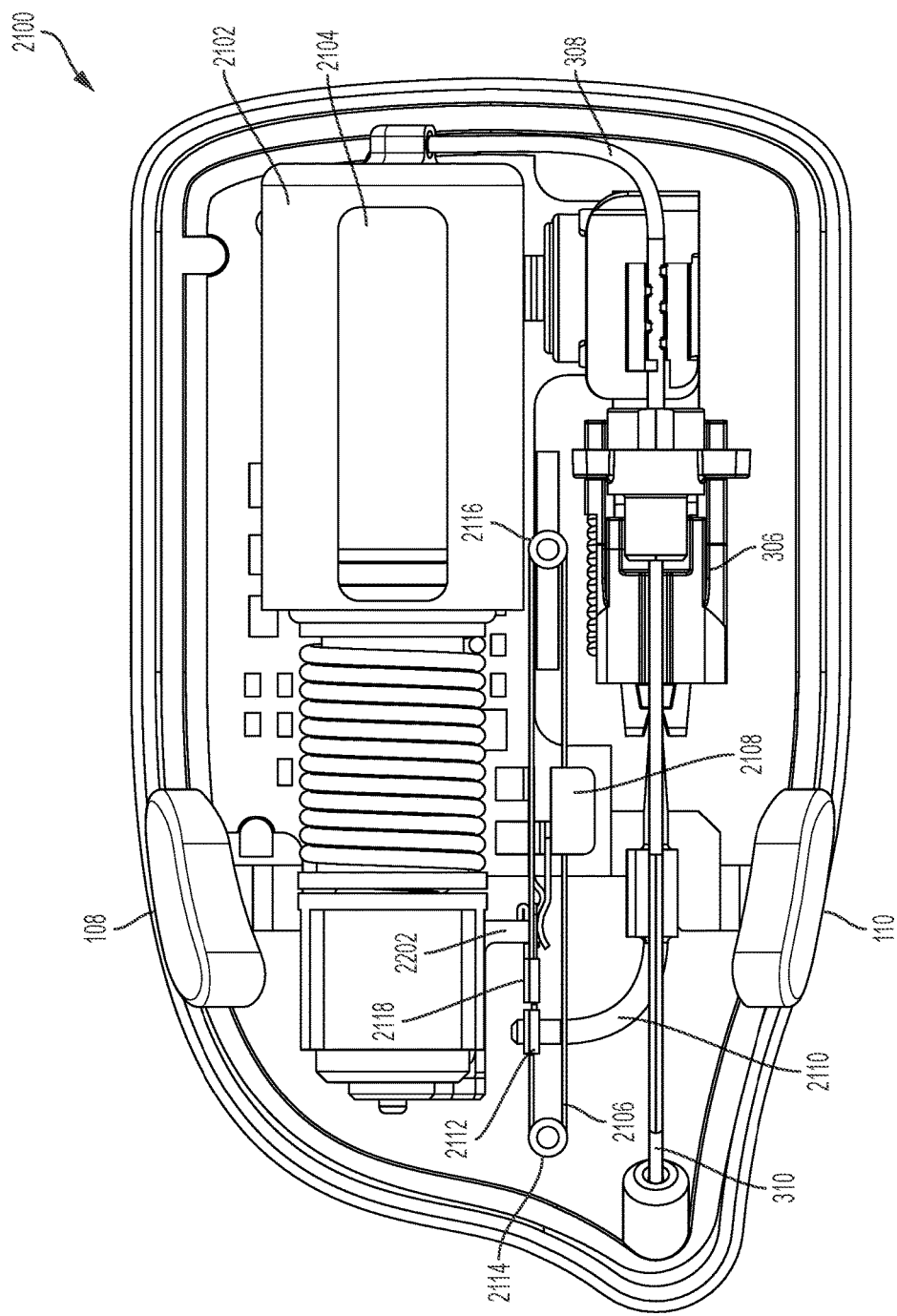
FIG. 22 illustrates a first overhead view of the drug delivery device depicted in FIG. 21.

FIG. 22 illustrates an overhead view of the drug delivery device 2100 depicted in FIG. 21. As shown in FIG. 22, the release lever 2112 can be coupled to the release bar 2110. The release lever 2118 can be coupled to an extension or release bar 2202. The release bar 2202 can be coupled to the release component 326 and/or can be coupled to one or more components for triggering movement of the plunger 504.

To activate the drug delivery device 2100 once it has been filled with a desired amount of liquid drug or other agent, the patient can engage/actuate the first and second user interaction features 108 and 110. The first and second user interaction features 108 and 110 can be engaged/actuated (e.g., pressing, sliding) in a predetermined manner to activate the drug delivery device 210. In various embodiments, the first and second user interaction features 108 and 110 can be engaged sequentially or approximately simultaneously.

Once at least one or both of the first and second user interaction features 108 and 110 have been engaged, a controller (not shown in FIG. 21 for simplicity) coupled to the PCBA and coupled to the first and second user interaction features 108 and 110, can energize the SMA wire 2106. In various embodiments, the controller can cause the power source to energize the portion of the SMA wire 2106 between the first connector 2114 and the release lever 2112. When this portion of the SMA wire 2106 is energized, the SMA wire 2106 between the first connector 2114 and the release lever 2112 can contract and/or change shape. When this portion of the SMA wire 2106 contracts, the release lever 2112 can be caused to push down on the release bar 2110, thereby triggering the needle insertion component 306. As a result, the end or tip of the needle 310 is inserted into the patient.

In various embodiments, after activation of the needle insertion component 306, the controller can cause the power source to energize the portion of the SMA wire between the release lever 2118 and the second connector 2116. When this portion of the SMA wire 2106 is energized, the SMA wire 2106 between the release lever 2118 and the second connector 2116 can contract and/or change shape. When this portion of the SMA wire 2106 contracts, the release lever 2118 can be moved in a predetermined direction to become decoupled or detached from the release bar 2202. Once the release lever 2118 is decoupled from the release bar 2202, the release bar 2202 is no longer restricted from moving and can therefore rotate, triggering initial movement of the plunger 504.

Figure 23:
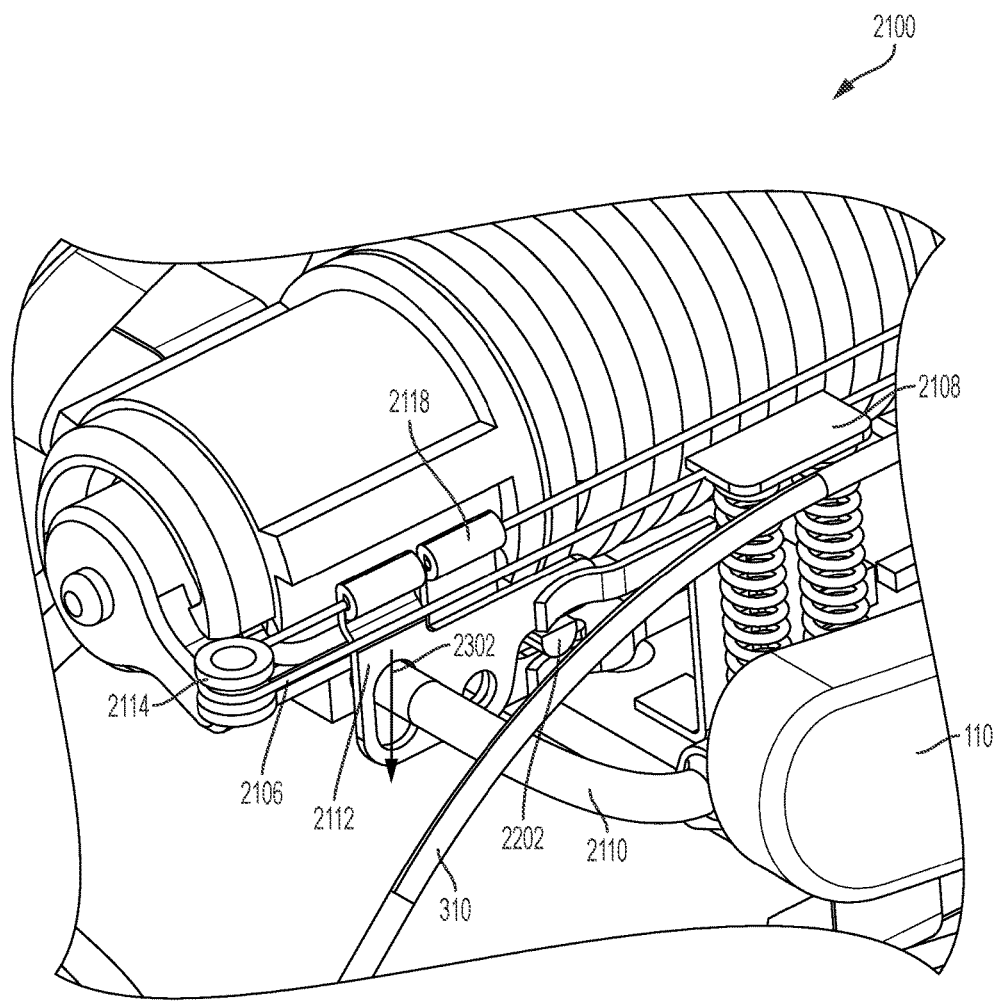
FIG. 23 illustrates a first isometric view of a portion of the drug delivery device depicted in FIG. 21.

FIG. 23 illustrates a portion of the components of the drug delivery device 2100 depicted in FIG. 22. In particular, FIG. 23 shows the interaction of the release lever 2112 and the release bar 2110. As shown in FIG. 23, the contraction of the SMA wire 2106 between the release lever 2112 and the connector 2114 can cause the release lever 2112 to push down on the release bar 2110 in a direction 2302. As a result, the release bar 2110 can be caused to rotate in a predetermined manner that activates the needle insertion component 306.

After the needle insertion component 306 is triggered and access to the patient is provided by the needle 310, the release bar 2202 can be caused to move (e.g., rotated) to thereby initiate movement of the plunger 504. Activation of the plunger 504 can be triggered by patient action (e.g., by engagement/actuation of the second user interaction feature 110) or by action of the controller operating according to a predetermined timing sequence (e.g., triggering the energizing of the SMA wire 2106 a predetermined amount of time after the needle insertion component 306 is activated). Under either scenario, activation can be effectuated by energizing a second side of the SMA wire 2106 as described herein.

Figure 24:
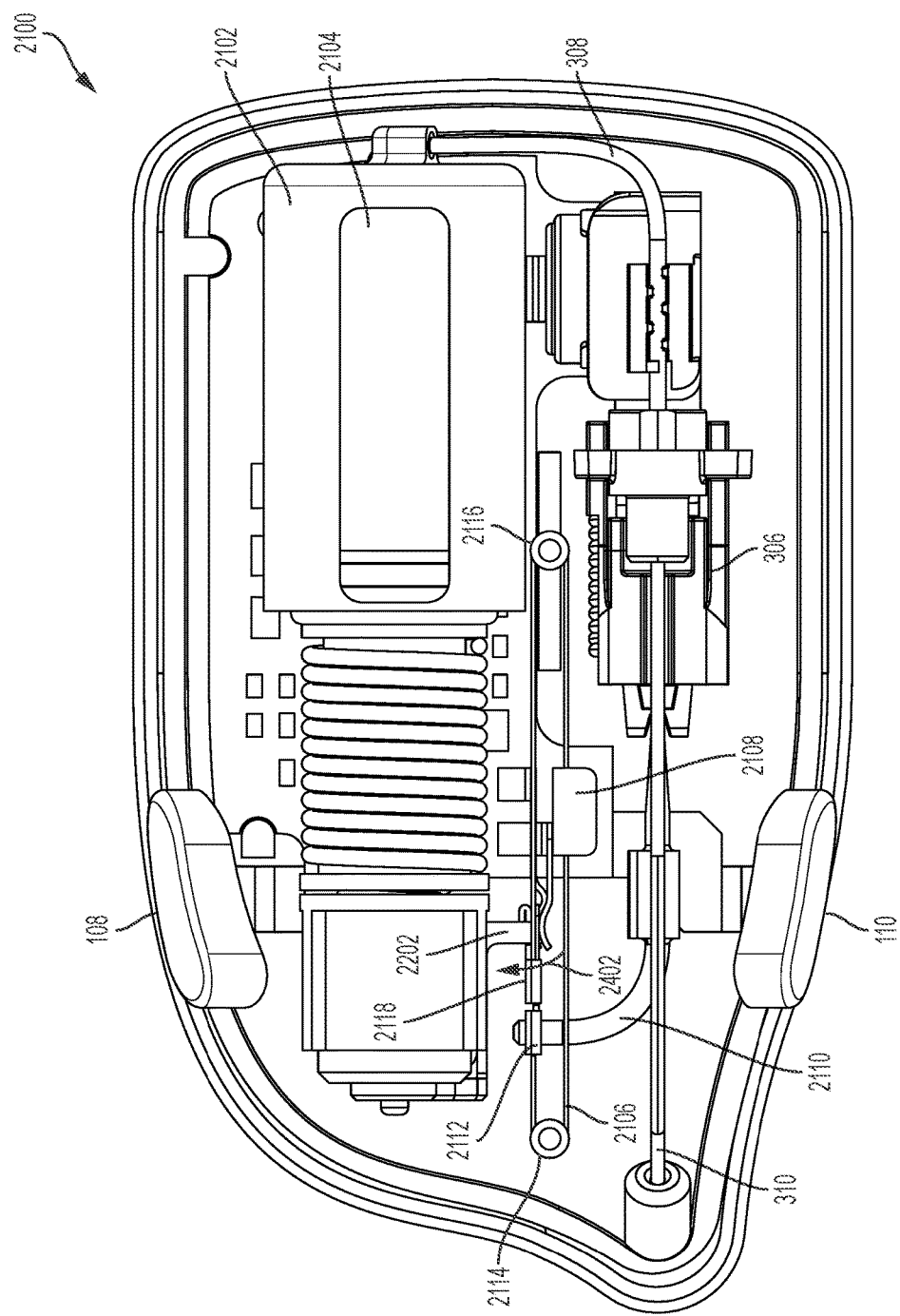
FIG. 24 illustrates a second overhead view of the drug delivery device depicted in FIG. 21.

FIG. 24 illustrates a second overhead view of the drug delivery device 2100 depicted in FIG. 21. FIG. 24 shows a direction of rotation 2402 of the release bar 2202 when the release bar 2202 is decoupled from the release lever 2118. Rotation of the release bar 2202 can cause the plunger 504 to begin expelling the liquid drug or other agent from the drug container 2102, as previously described.

Figure 25:
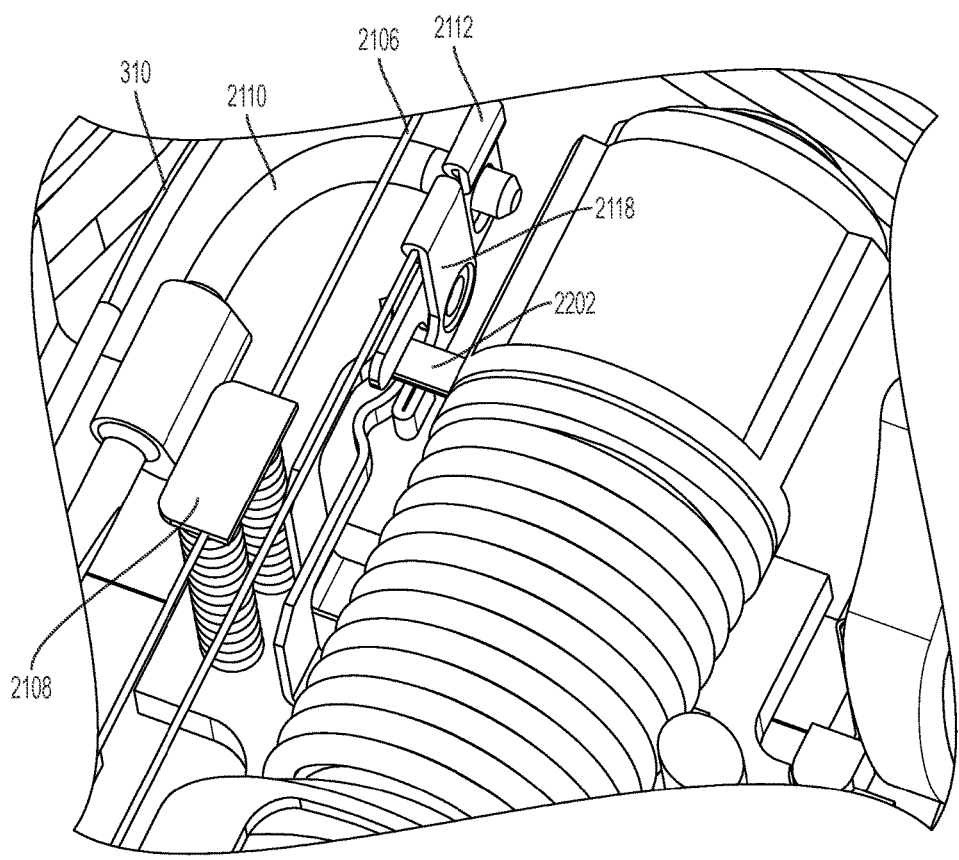
FIG. 25 illustrates a detailed isometric view of a portion of the drug delivery device depicted in FIG. 21.

FIG. 25 illustrates a portion of the components of the drug delivery device 2100 depicted in FIG. 24. In particular, FIG. 25 shows the interaction of the release lever 2112 and the interaction of the release bar 2110 as well as the interaction between the release lever 2118 and the release bar 2202.

The following examples pertain to further embodiments:

Example 1 is a variable fill drug delivery device comprising a container configured to store a user-selectable amount of a therapeutic agent, a plunger positioned in the container, and an infusion engine coupled to the plunger, the infusion engine configured to retain the plunger prior to activation of the variable fill drug delivery device, the infusion engine configured release the plunger after activation of the variable fill drug delivery device and to drive the plunger from a first position within the container to a second position within the container to expel the user-selectable amount of the therapeutic agent from the container for delivery to a patient.

Example 2 is an extension of Example 1 or any other example disclosed herein, wherein the user-selectable amount of the therapeutic agent is variable.

Example 3 is an extension of Example 1 or any other example disclosed herein, wherein the user-selectable amount of the therapeutic agent is less than a total fixed amount of the therapeutic agent that the container is configured to store.

Example 4 is an extension of Example 1 or any other example disclosed herein, wherein the infusion engine comprises a flexure beam housing attached to the plunger by a first plunger latch and a second plunger latch.

Example 5 is an extension of Example 4 or any other example disclosed herein, wherein the first plunger latch is attached to a first depending tab portion of a first arm of the plunger and the second plunger latch is attached to a second depending tab portion of a second arm of the plunger.

Example 6 is an extension of Example 5 or any other example disclosed herein, wherein the first plunger latch is positioned at an end of a first arm of the flexure beam housing and the second plunger latch is positioned at an end of a second arm of the flexure beam housing.

Example 7 is an extension of Example 6 or any other example disclosed herein, wherein the infusion engine further comprises a release coupler positioned between the first and second arms of the flexure beam housing, an end of the release coupler attached to the plunger.

Example 8 is an extension of Example 7 or any other example disclosed herein, wherein the release coupler is coupled to a fixed thrust component.

Example 9 is an extension of Example 8 or any other example disclosed herein, wherein the fixed thrust component comprises a base and a spline shaft extending from the base, wherein the release coupler is coupled to the spline shaft of the fixed thrust component, the release coupler and the spline shaft forming a slip joint.

Example 10 is an extension of Example 9 or any other example disclosed herein, wherein the base of the fixed thrust component is coupled to a release component.

Example 11 is an extension of Example 10 or any other example disclosed herein, wherein the infusion engine further comprises a clutch spring positioned around the base of the fixed thrust component and coupled to the flexure beam housing.

Example 12 is an extension of Example 11 or any other example disclosed herein, wherein the clutch spring is configured to attach to the base of the fixed thrust component after the container is filled with the user-selectable amount of the therapeutic agent.

Example 13 is an extension of Example 12 or any other example disclosed herein, wherein the clutch spring is configured to attach to the base of the fixed thrust component after the patient engages a first user interaction component.

Example 14 is an extension of Example 12 or any other example disclosed herein, wherein the clutch spring is configured to attach to the base of the fixed thrust component after an on-body interlock of the variable fill drug delivery device is engaged.

Example 15 is an extension of Example 11 or any other example disclosed herein, wherein the clutch spring is a radial torsion spring.

Example 16 is an extension of Example 11 or any other example disclosed herein, wherein the infusion engine further comprises a first compression spring positioned around the first and second arms of the flexure beam housing.

Example 17 is an extension of Example 16 or any other example disclosed herein, wherein the infusion engine further comprises a spring cap positioned around a portion of the first compression spring, an end of the spring cap adjacent to the plunger.

Example 18 is an extension of Example 17 or any other example disclosed herein, wherein the spring cap is positioned over the first and second arms of the plunger.

Example 19 is an extension of Example 18 or any other example disclosed herein, wherein the infusion engine further comprises a second compression spring positioned around the spring cap.

Example 20 is an extension of Example 19 or any other example disclosed herein, an end of the second compression spring adjacent to the plunger and positioned over the end of the spring cap.

Example 21 is an extension of Example 20 or any other example disclosed herein, wherein the release component is configured to rotate when the variable fill drug delivery device is activated.

Example 22 is an extension of Example 21 or any other example disclosed herein, wherein the fixed thrust component is configured to rotate about a central axis of the fixed thrust component when the release component rotates.

Example 23 is an extension of Example 22 or any other example disclosed herein, wherein the release coupler is configured to rotate with the spline shaft of the fixed thrust member.

Example 24 is an extension of Example 23 or any other example disclosed herein, wherein the first plunger latch is configured to disengage from the first depending tab portion of the first arm of the plunger and the second plunger latch is configured to detach from the second depending tab portion of the second arm of the plunger to release the plunger when the release coupler rotates.

Example 25 is an extension of Example 24 or any other example disclosed herein, wherein the release coupler is shaped to have a first length in a first direction and a second length in a second direction perpendicular to the first direction, wherein the first length is larger than the second length.

Example 26 is an extension of Example 24 or any other example disclosed herein, wherein the release coupler is configured to not press against the first and second arms of the flexure beam housing after rotating.

Example 27 is an extension of Example 26 or any other example disclosed herein, wherein the first and second compression springs are configured to expand when the first plunger latch is disengaged from the first depending tab portion of the first arm of the plunger and the second plunger latch is disengaged from the second depending tab portion of the second arm of the plunger.

Example 28 is an extension of Example 27 or any other example disclosed herein, wherein the first and second compression springs are configured to drive the plunger from the first position within the container to the second position within the container as the first and second compressions springs expand.

Example 29 is an extension of Example 28 or any other example disclosed herein, wherein the first and second compressions springs are arranged in series.

Example 30 is an extension of Example 28 or any other example disclosed herein, wherein the first and second compressions springs have substantially the same spring constant values.

Example 31 is an extension of Example 28 or any other example disclosed herein, wherein the expelled therapeutic agent is provided to a needle.

The following examples pertain to additional further embodiments:

Example 1 is a method for expelling a user-selectable amount of a therapeutic agent stored in a container of a variable fill drug delivery device comprising engaging a first user interaction component, rotating a fixed thrust member responsive to engaging the first user interaction component, disengaging a first plunger latch from a first depending portion of a first arm of a plunger and disengaging a second plunger latch from a second depending portion of a second arm of the plunger responsive to rotating the fixed thrust member, and expanding a first compression spring responsive to disengaging the first and second plunger latches from the first and second depending portions of the first and second arms of the plunger, respectively, to drive the plunger into the container to expel the user-selectable amount of the therapeutic agent from the container for delivery to a patient.

Example 2 is an extension of Example 1 or any other example disclosed herein, further comprising engaging a second user interaction component prior to engaging the first user interaction component.

Example 3 is an extension of Example 2 or any other example disclosed herein, wherein engaging the second user interaction component unlocks the first user interaction component.

Example 4 is an extension of Example 3 or any other example disclosed herein, further comprising rotating a deadbolt component restricting movement of the first user interaction component responsive to engaging the second user interaction component.

Example 5 is an extension of Example 1 or any other example disclosed herein, further comprising inserting a needle into the patient responsive to engaging the first user interaction component.

Example 6 is an extension of Example 1 or any other example disclosed herein, further comprising rotating a release component coupled to the fixed thrust member responsive to engaging the first user interaction component.

Example 7 is an extension of Example 6 or any other example disclosed herein, further comprising rotating a release coupler coupled to the fixed thrust member responsive to rotating the fixed thrust member, the release coupler positioned between the first and second plunger latches.

Example 8 is an extension of Example 1 or any other example disclosed herein, further comprising expanding a second compression spring responsive to disengaging the first and second plunger latches from the first and second depending portions of the first and second arms of the plunger, respectively.

Example 9 is an extension of Example 8 or any other example disclosed herein, further comprising applying a force to the plunger from at least one of the first and the second compression springs to drive the plunger towards an end of the container.

Example 10 is an extension of Example 1 or any other example disclosed herein, further comprising providing the expelled user-selectable amount of the therapeutic agent to a needle.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A variable fill drug delivery device, comprising:
a container configured to store a user-selectable amount of a therapeutic agent;
a plunger positioned in the container; and
an infusion engine coupled to the plunger, the infusion engine configured to retain the plunger prior to activation of the variable fill drug delivery device, the infusion engine configured to release the plunger after activation of the variable fill drug delivery device and to drive the plunger from a first position within the container to a second position within the container to expel the user-selectable amount of the therapeutic agent from the container for delivery to a patient,
wherein the infusion engine comprises a flexure beam housing attached to the plunger by a first plunger latch and a second plunger latch,
wherein the first plunger latch is attached to a first depending tab portion of a first arm of the plunger and the second plunger latch is attached to a second depending tab portion of a second arm of the plunger,
wherein the first plunger latch is positioned at an end of a first arm of the flexure beam housing and the second plunger latch is positioned at an end of a second arm of the flexure beam housing,
wherein the infusion engine further comprises a release coupler positioned between the first and second arms of the flexure beam housing, an end of the release coupler attached to the plunger,
wherein the release coupler is coupled to a fixed thrust component,
wherein the fixed thrust component comprises a base and a spline shaft extending from the base, wherein the release coupler is coupled to the spline shaft of the fixed thrust component, the release coupler and the spline shaft forming a slip joint,
wherein the base of the fixed thrust component is coupled to a release component,
wherein the infusion engine further comprises a clutch spring positioned around the base of the fixed thrust component and coupled to the flexure beam housing,
wherein the infusion engine further comprises a first compression spring positioned around the first and second arms of the flexure beam housing.

2. The variable fill drug delivery device of claim 1, wherein the infusion engine further comprises a spring cap positioned around a portion of the first compression spring, an end of the spring cap adjacent to the plunger.

3. The variable fill drug delivery device of claim 2, wherein the spring cap is positioned over the first and second arms of the plunger.

4. The variable fill drug delivery device of claim 3, wherein the infusion engine further comprises a second compression spring positioned around the spring cap.

5. The variable fill drug delivery device of claim 4, wherein an end of the second compression spring is adjacent to the plunger and positioned over the end of the spring cap.

6. The variable fill drug delivery device of claim 5, wherein the release component is configured to rotate when the variable fill drug delivery device is activated.

7. The variable fill drug delivery device of claim 6, wherein the fixed thrust component is configured to rotate about a central axis of the fixed thrust component when the release component rotates.

8. The variable fill drug delivery device of claim 7, wherein the release coupler is configured to rotate with the spline shaft of the fixed thrust member.

9. The variable fill drug delivery device of claim 8, wherein the first plunger latch is configured to disengage from the first depending tab portion of the first arm of the plunger and the second plunger latch is configured to detach from the second depending tab portion of the second arm of the plunger to release the plunger when the release coupler rotates.

10. The variable fill drug delivery device of claim 9, wherein the release coupler is shaped to have a first length in a first direction and a second length in a second direction perpendicular to the first direction, wherein the first length is larger than the second length.

11. The variable fill drug delivery device of claim 9, wherein the release coupler is configured to not press against the first and second arms of the flexure beam housing after rotating.

12. The variable fill drug delivery device of claim 11, wherein the first and second compression springs are configured to expand when the first plunger latch is disengaged from the first depending tab portion of the first arm of the plunger and the second plunger latch is disengaged from the second depending tab portion of the second arm of the plunger.

13. The variable fill drug delivery device of claim 12, wherein the first and second compression springs are configured to drive the plunger from the first position within the container to the second position within the container as the first and second compressions springs expand.

14. The variable fill drug delivery device of claim 13, wherein the first and second compressions springs are arranged in series.

15. The variable fill drug delivery device of claim 13, wherein the first and second compressions springs have substantially the same spring constant values.

16. The variable fill drug delivery device of claim 13, wherein the expelled user-selectable amount of the therapeutic agent is provided to a needle.

17. The variable fill drug delivery device of claim 1, wherein the user-selectable amount of the therapeutic agent is less than a total fixed amount of the therapeutic agent that the container is configured to store.

18. The variable fill drug delivery device of claim 1, wherein the clutch spring is configured to attach to the base of the fixed thrust component after the container is filled with the user-selectable amount of the therapeutic agent.

19. The variable fill drug delivery device of claim 1, wherein the clutch spring is configured to attach to the base of the fixed thrust component after the patient engages a first user interaction component.

20. The variable fill drug delivery device of claim 1, wherein the clutch spring is configured to attach to the base of the fixed thrust component after an on-body interlock of the variable fill drug delivery device is engaged.

21. The variable fill drug delivery device of claim 1, wherein the clutch spring is a radial torsion spring.

\* \* \* \* \*